United States Patent
Takayama et al.

(10) Patent No.: US 12,291,554 B2
(45) Date of Patent: May 6, 2025

(54) MODIFIED ACTIVIN A

(71) Applicants: Mitsubishi Chemical Corporation, Tokyo (JP); UniBio Corporation, Niigata (JP)

(72) Inventors: Hidehito Takayama, Tokyo (JP); Risa Watanabe, Tokyo (JP); Yutaka Takemoto, Tokyo (JP); Hiroyuki Tanaka, Tokyo (JP); Hiroshi Kawabata, Tokyo (JP); Kyoji Yoshinaka, Niigata (JP)

(73) Assignees: Mitsubishi Chemical Corporation, Tokyo (JP); UniBio Corporation, Niigata (JP)

( * ) Notice: Subject to any disclaimer, the term of this patent is extended or adjusted under 35 U.S.C. 154(b) by 1000 days.

(21) Appl. No.: 17/321,049

(22) Filed: May 14, 2021

(65) Prior Publication Data

US 2021/0269495 A1 Sep. 2, 2021

Related U.S. Application Data

(63) Continuation of application No. PCT/JP2019/044744, filed on Nov. 14, 2019.

(30) Foreign Application Priority Data

Nov. 15, 2018 (JP) ................................. 2018-214630

(51) Int. Cl.
 C12P 21/02 (2006.01)
 A01H 5/00 (2018.01)
 C07K 14/52 (2006.01)
 C12N 15/63 (2006.01)
 C12N 15/82 (2006.01)

(52) U.S. Cl.
 CPC .......... C07K 14/52 (2013.01); C12N 15/8257 (2013.01)

(58) Field of Classification Search
 CPC ... C12N 15/8257; C07K 14/46; C07K 14/495
 See application file for complete search history.

(56) References Cited

U.S. PATENT DOCUMENTS

| 11,401,311 B2 * | 8/2022 | Hirano ................. C07K 14/495 |
| 2003/0033637 A1 | 2/2003 | Oishi et al. |
| 2005/0015830 A1 | 1/2005 | Dorokhov et al. |
| 2021/0017245 A1 * | 1/2021 | Hirano ................. C07K 14/495 |

FOREIGN PATENT DOCUMENTS

| JP | 2005-501558 A | | 1/2005 |
| JP | 102131515 A | | 7/2011 |
| WO | WO 02/099067 A2 | | 12/2002 |
| WO | 086845 | * | 9/2005 |
| WO | WO 2009/158033 A2 | | 12/2009 |
| WO | WO 2017/088027 A1 | | 6/2017 |

OTHER PUBLICATIONS

Extended European Search Report issued Feb. 28, 2022 in European Patent Application No. 19884923.4, 8 pages.
"Activin Beta-A Chain" Database UniProt [Online], Database accession No. G1QS95, XP055890584, Oct. 19, 2011, 2 pages.
Lindblad-Toh Kerstin, et al., "Activin Beta-A Chain" Database UniProt [Online], Database accession No. G1PZW6, XP055890614, Oct. 19, 2011, 1 page.
Di Palma F. et al., "Activin Beta-A Chain" Database UniProt [Online], Database accession No. G3U4E6, XP055890656, Nov. 16, 2011, 2 pages.
Sainsbury et al., "Transient expressions of synthetic biology in plants", Current Opinion in Plant Biology, 2014, 19:1-7.
Mandal MK. et al., "Tackling Unwanted Proteolysis in Plant Production Hosts Used for Molecular Farming", Frontiers in Plant Science, Mar. 2015, vol. 7, 267.
Pillary P. et al., "Proteolysis of recombinant proteins in bioengineered plant cells", Bioengineered, 5: 1, 15-20, 2014.
Wang X. et al., "Structure and activation of pro-activin A", Nature Communication, Jul. 4, 2016, 12052.
Fischer W.H. et al., "Residues in the C-terminal region of activin A determine specificity for follistatin and type II receptor binding", Journal of Endocrinology, Jan. 2003, vol. 176, No. 1, 61-68.
International Search Report issued for PCT/JP2019/044744 dated Jan. 28, 2020.
Combined Chinese Office Action and Search Report issued Nov. 1, 2023 in Chinese Patent Application No. 201980074789.6, 7 pages.

* cited by examiner

Primary Examiner — Maryam Monshipouri
(74) Attorney, Agent, or Firm — Oblon, McClelland, Maier & Neustadt, L.L.P.

(57) ABSTRACT

The purpose of the present invention is to provide a modified activin A.
The present invention provides activin A comprising a modified proregion.

12 Claims, 2 Drawing Sheets

Specification includes a Sequence Listing.

[Fig. 1]
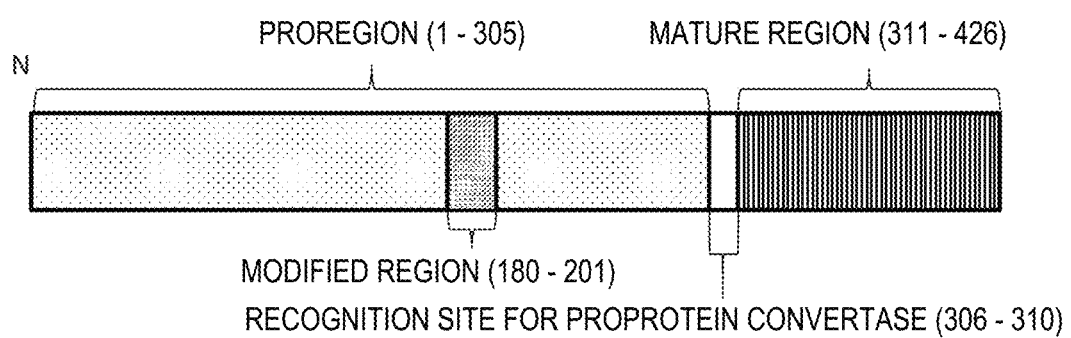

[Fig. 2]
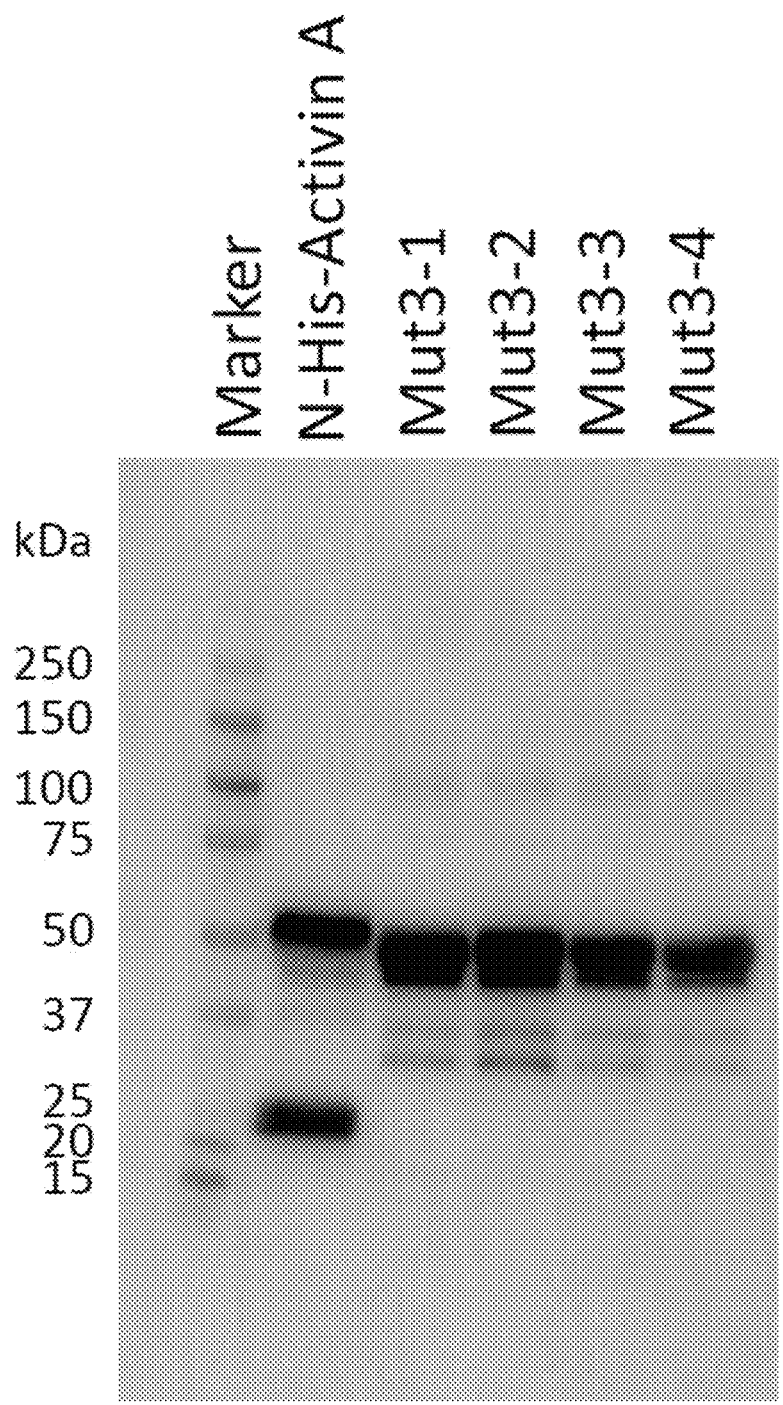

SEQUENCE LISTING

```
<160> NUMBER OF SEQ ID NOS: 39

<210> SEQ ID NO 1
<211> LENGTH: 426
<212> TYPE: PRT
<213> ORGANISM: Homo sapiens

<400> SEQUENCE: 1

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
```

```
                    165                 170                 175
Gln Gln Gln Lys His Pro Gln Gly Ser Leu Asp Thr Gly Glu Glu Ala
                180                 185                 190

Glu Glu Val Gly Leu Lys Gly Glu Arg Ser Glu Leu Leu Leu Ser Glu
            195                 200                 205

Lys Val Val Asp Ala Arg Lys Ser Thr Trp His Val Phe Pro Val Ser
        210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Glu Glu Gly Gly Lys Lys Lys
                260                 265                 270

Gly Gly Gly Glu Gly Gly Ala Gly Ala Asp Glu Lys Glu Gln Ser
                275                 280                 285

His Arg Pro Phe Leu Met Leu Gln Ala Arg Gln Ser Glu Asp His Pro
            290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
                340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
        370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
                420                 425

<210> SEQ ID NO 2
<211> LENGTH: 424
<212> TYPE: PRT
<213> ORGANISM: Mus musculus

<400> SEQUENCE: 2

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ser Ala
                20                  25                  30

Pro Asp Cys Pro Ser Cys Ala Leu Ala Thr Leu Pro Lys Asp Gly Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110
```

Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
        130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Asp Glu Ala
            180                 185                 190

Glu Glu Met Gly Leu Lys Gly Glu Arg Ser Glu Leu Leu Leu Ser Glu
        195                 200                 205

Lys Val Val Asp Ala Arg Lys Ser Thr Trp His Ile Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Val Asp Gly Asp Gly Lys Lys Lys
            260                 265                 270

Asp Gly Ser Asp Gly Gly Leu Glu Glu Glu Lys Glu Gln Ser His Arg
        275                 280                 285

Pro Phe Leu Met Leu Gln Ala Arg Gln Ser Glu Asp His Pro His Arg
        290                 295                 300

Arg Arg Arg Arg Gly Leu Glu Cys Asp Gly Lys Val Asn Ile Cys Cys
305                 310                 315                 320

Lys Lys Gln Phe Phe Val Ser Phe Lys Asp Ile Gly Trp Asn Asp Trp
                325                 330                 335

Ile Ile Ala Pro Ser Gly Tyr His Ala Asn Tyr Cys Glu Gly Glu Cys
            340                 345                 350

Pro Ser His Ile Ala Gly Thr Ser Gly Ser Ser Leu Ser Phe His Ser
        355                 360                 365

Thr Val Ile Asn His Tyr Arg Met Arg Gly His Ser Pro Phe Ala Asn
        370                 375                 380

Leu Lys Ser Cys Cys Val Pro Thr Lys Leu Arg Pro Met Ser Met Leu
385                 390                 395                 400

Tyr Tyr Asp Asp Gly Gln Asn Ile Ile Lys Lys Asp Ile Gln Asn Met
                405                 410                 415

Ile Val Glu Glu Cys Gly Cys Ser
            420

<210> SEQ ID NO 3
<211> LENGTH: 424
<212> TYPE: PRT
<213> ORGANISM: Rattus norvegicus

<400> SEQUENCE: 3

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ala Ala
            20                  25                  30

Pro Asp Cys Pro Ser Cys Ala Leu Ala Thr Leu Pro Lys Asp Gly Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
 65                  70                  75                  80

Ala Ala Leu Leu Asn Ala Ile Arg Lys Leu His Val Gly Lys Val Gly
                 85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
145                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Met Gly Asp Glu Ala
            180                 185                 190

Glu Glu Met Gly Leu Lys Gly Glu Arg Ser Glu Leu Leu Leu Ser Glu
        195                 200                 205

Lys Val Val Asp Ala Arg Lys Ser Thr Trp His Ile Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Val Asp Gly Asp Gly Lys Lys Lys
            260                 265                 270

Asp Gly Ser Asp Gly Gly Leu Glu Glu Glu Lys Glu Gln Ser His Arg
        275                 280                 285

Pro Phe Leu Met Leu Gln Ala Arg Gln Ser Glu Asp His Pro His Arg
    290                 295                 300

Arg Arg Arg Arg Gly Leu Glu Cys Asp Gly Lys Val Asn Ile Cys Cys
305                 310                 315                 320

Lys Lys Gln Phe Phe Val Ser Phe Lys Asp Ile Gly Trp Asn Asp Trp
                325                 330                 335

Ile Ile Ala Pro Ser Gly Tyr His Ala Asn Tyr Cys Glu Gly Glu Cys
            340                 345                 350

Pro Ser His Ile Ala Gly Thr Ser Gly Ser Ser Leu Ser Phe His Ser
        355                 360                 365

Thr Val Ile Asn His Tyr Arg Met Arg Gly His Ser Pro Phe Ala Asn
    370                 375                 380

Leu Lys Ser Cys Cys Val Pro Thr Lys Leu Arg Pro Met Ser Met Leu
385                 390                 395                 400

Tyr Tyr Asp Asp Gly Gln Asn Ile Ile Lys Lys Asp Ile Gln Asn Met
                405                 410                 415

Ile Val Glu Glu Cys Gly Cys Ser
            420

<210> SEQ ID NO 4
<211> LENGTH: 305
<212> TYPE: PRT
<213> ORGANISM: Homo sapiens

<400> SEQUENCE: 4

Met Pro Leu Leu Trp Leu Arg Gly Phe Leu Leu Ala Ser Cys Trp Ile

```
    1               5                   10                  15
Ile Val Arg Ser Ser Pro Thr Pro Gly Ser Glu Gly His Ser Ala Ala
                20                  25                  30

Pro Asp Cys Pro Ser Cys Ala Leu Ala Ala Leu Pro Lys Asp Val Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
                100                 105                 110

Met Asn Glu Leu Met Glu Gln Thr Ser Glu Ile Ile Thr Phe Ala Glu
                115                 120                 125

Ser Gly Thr Ala Arg Lys Thr Leu His Phe Glu Ile Ser Lys Glu Gly
                130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
                180                 185                 190

Glu Glu Val Gly Leu Lys Gly Glu Arg Ser Glu Leu Leu Leu Ser Glu
                195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
                260                 265                 270

Gly Gly Gly Glu Gly Gly Ala Gly Ala Asp Glu Glu Lys Glu Gln Ser
                275                 280                 285

His Arg Pro Phe Leu Met Leu Gln Ala Arg Gln Ser Glu Asp His Pro
    290                 295                 300

His
305

<210> SEQ ID NO 5
<211> LENGTH: 303
<212> TYPE: PRT
<213> ORGANISM: Mus musculus

<400> SEQUENCE: 5

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ser Ala
                20                  25                  30

Pro Asp Cys Pro Ser Cys Ala Leu Ala Thr Leu Pro Lys Asp Gly Pro
            35                  40                  45

Asn Ser Gln Pro Glu Met Val Glu Ala Val Lys Lys His Ile Leu Asn
        50                  55                  60
```

```
Met Leu His Leu Lys Lys Arg Pro Asp Val Thr Gln Pro Val Pro Lys
 65                  70                  75                  80

Ala Ala Leu Leu Asn Ala Ile Arg Lys Leu His Val Gly Lys Val Gly
                 85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Asp Glu Ala
            180                 185                 190

Glu Glu Met Gly Leu Lys Gly Glu Arg Ser Glu Leu Leu Leu Ser Glu
        195                 200                 205

Lys Val Val Asp Ala Arg Lys Ser Thr Trp His Ile Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Val Asp Gly Asp Gly Lys Lys Lys
            260                 265                 270

Asp Gly Ser Asp Gly Gly Leu Glu Glu Glu Lys Glu Gln Ser His Arg
        275                 280                 285

Pro Phe Leu Met Leu Gln Ala Arg Gln Ser Glu Asp His Pro His
        290                 295                 300

<210> SEQ ID NO 6
<211> LENGTH: 303
<212> TYPE: PRT
<213> ORGANISM: Rattus norvegicus

<400> SEQUENCE: 6

Met Pro Leu Leu Trp Leu Arg Gly Phe Leu Leu Ala Ser Cys Trp Ile
  1               5                  10                  15

Ile Val Arg Ser Ser Pro Thr Pro Gly Ser Glu Gly His Gly Ala Ala
                 20                  25                  30

Pro Asp Cys Pro Ser Cys Ala Leu Ala Thr Leu Pro Lys Asp Gly Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
 65                  70                  75                  80

Ala Ala Leu Leu Asn Ala Ile Arg Lys Leu His Val Gly Lys Val Gly
                 85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
130                 135                 140
```

```
Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Met Gly Asp Glu Ala
            180                 185                 190

Glu Glu Met Gly Leu Lys Gly Glu Arg Ser Glu Leu Leu Leu Ser Glu
            195                 200                 205

Lys Val Val Asp Ala Arg Lys Ser Thr Trp His Ile Phe Pro Val Ser
        210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Glu Val Asp Gly Asp Gly Lys Lys Lys
            260                 265                 270

Asp Gly Ser Asp Gly Gly Leu Glu Glu Glu Lys Glu Gln Ser His Arg
        275                 280                 285

Pro Phe Leu Met Leu Gln Ala Arg Gln Ser Glu Asp His Pro His
    290                 295                 300
```

```
<210> SEQ ID NO 7
<211> LENGTH: 5
<212> TYPE: PRT
<213> ORGANISM: Artificial
<220> FEATURE:
<223> OTHER INFORMATION: Synthetic peptide

<400> SEQUENCE: 7

Arg Arg Arg Arg Arg
1               5
```

```
<210> SEQ ID NO 8
<211> LENGTH: 116
<212> TYPE: PRT
<213> ORGANISM: Artificial
<220> FEATURE:
<223> OTHER INFORMATION: Synthetic peptide

<400> SEQUENCE: 8

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile Ala Pro
            20                  25                  30

Ser Gly Tyr His Ala Asn Tyr Cys Glu Gly Glu Cys Pro Ser His Ile
        35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
65                  70                  75                  80

Cys Val Pro Thr Lys Leu Arg Pro Met Ser Met Leu Tyr Tyr Asp Asp
                85                  90                  95

Gly Gln Asn Ile Ile Lys Lys Asp Ile Gln Asn Met Ile Val Glu Glu
            100                 105                 110

Cys Gly Cys Ser
        115
```

```
<210> SEQ ID NO 9
<211> LENGTH: 287
<212> TYPE: PRT
<213> ORGANISM: Artificial
<220> FEATURE:
<223> OTHER INFORMATION: Synthetic peptide

<400> SEQUENCE: 9

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Glu Arg Ser Glu Leu Leu Leu Ser Glu Lys Val
            180                 185                 190

Val Asp Ala Arg Lys Ser Thr Trp His Val Phe Pro Val Ser Ser Ser
        195                 200                 205

Ile Gln Arg Leu Leu Asp Gln Gly Lys Ser Ser Leu Asp Val Arg Ile
    210                 215                 220

Ala Cys Glu Gln Cys Gln Glu Ser Gly Ala Ser Leu Val Leu Leu Gly
225                 230                 235                 240

Lys Lys Lys Lys Lys Glu Glu Glu Gly Glu Lys Lys Lys Gly Gly
                245                 250                 255

Gly Glu Gly Gly Ala Gly Ala Asp Glu Glu Lys Glu Gln Ser His Arg
            260                 265                 270

Pro Phe Leu Met Leu Gln Ala Arg Gln Ser Glu Asp His Pro His
        275                 280                 285

<210> SEQ ID NO 10
<211> LENGTH: 285
<212> TYPE: PRT
<213> ORGANISM: Artificial
<220> FEATURE:
<223> OTHER INFORMATION: Synthetic peptide

<400> SEQUENCE: 10

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ser Ala
            20                  25                  30
```

Pro Asp Cys Pro Ser Cys Ala Leu Ala Thr Leu Pro Lys Asp Gly Pro
         35                  40                  45

Asn Ser Gln Pro Glu Met Val Glu Ala Val Lys Lys His Ile Leu Asn
 50                  55                  60

Met Leu His Leu Lys Lys Arg Pro Asp Val Thr Gln Pro Val Pro Lys
 65                  70                  75                  80

Ala Ala Leu Leu Asn Ala Ile Arg Lys Leu His Val Gly Lys Val Gly
                 85                  90                  95

Glu Asn Gly Tyr Val Glu Ile Glu Asp Asp Ile Gly Arg Arg Ala Glu
                100                 105                 110

Met Asn Glu Leu Met Glu Gln Thr Ser Glu Ile Ile Thr Phe Ala Glu
                115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Glu Arg Ser Glu Leu Leu Leu Ser Glu Lys Val
                180                 185                 190

Val Asp Ala Arg Lys Ser Thr Trp His Ile Phe Pro Val Ser Ser Ser
    195                 200                 205

Ile Gln Arg Leu Leu Asp Gln Gly Lys Ser Ser Leu Asp Val Arg Ile
    210                 215                 220

Ala Cys Glu Gln Cys Gln Glu Ser Gly Ala Ser Leu Val Leu Leu Gly
225                 230                 235                 240

Lys Lys Lys Lys Lys Glu Val Asp Gly Asp Gly Lys Lys Asp Gly
                245                 250                 255

Ser Asp Gly Gly Leu Glu Glu Glu Lys Glu Gln Ser His Arg Pro Phe
                260                 265                 270

Leu Met Leu Gln Ala Arg Gln Ser Glu Asp His Pro His
                275                 280                 285

<210> SEQ ID NO 11
<211> LENGTH: 285
<212> TYPE: PRT
<213> ORGANISM: Artificial
<220> FEATURE:
<223> OTHER INFORMATION: Synthetic peptide

<400> SEQUENCE: 11

Met Pro Leu Leu Trp Leu Arg Gly Phe Leu Leu Ala Ser Cys Trp Ile
 1                5                  10                  15

Ile Val Arg Ser Ser Pro Thr Pro Gly Ser Glu Gly His Gly Ala Ala
                20                  25                  30

Pro Asp Cys Pro Ser Cys Ala Leu Ala Thr Leu Pro Lys Asp Gly Pro
         35                  40                  45

Asn Ser Gln Pro Glu Met Val Glu Ala Val Lys Lys His Ile Leu Asn
 50                  55                  60

Met Leu His Leu Lys Lys Arg Pro Asp Val Thr Gln Pro Val Pro Lys
 65                  70                  75                  80

Ala Ala Leu Leu Asn Ala Ile Arg Lys Leu His Val Gly Lys Val Gly
                 85                  90                  95

Glu Asn Gly Tyr Val Glu Ile Glu Asp Asp Ile Gly Arg Arg Ala Glu
                100                 105                 110

```
Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
        130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Glu Arg Ser Glu Leu Leu Leu Ser Glu Lys Val
            180                 185                 190

Val Asp Ala Arg Lys Ser Thr Trp His Ile Phe Pro Val Ser Ser Ser
        195                 200                 205

Ile Gln Arg Leu Leu Asp Gln Gly Lys Ser Ser Leu Asp Val Arg Ile
    210                 215                 220

Ala Cys Glu Gln Cys Gln Glu Ser Gly Ala Ser Leu Val Leu Leu Gly
225                 230                 235                 240

Lys Lys Lys Lys Lys Glu Val Asp Gly Asp Gly Lys Lys Lys Asp Gly
                245                 250                 255

Ser Asp Gly Gly Leu Glu Glu Glu Lys Glu Gln Ser His Arg Pro Phe
            260                 265                 270

Leu Met Leu Gln Ala Arg Gln Ser Glu Asp His Pro His
        275                 280                 285

<210> SEQ ID NO 12
<211> LENGTH: 288
<212> TYPE: PRT
<213> ORGANISM: Artificial
<220> FEATURE:
<223> OTHER INFORMATION: Synthetic peptide

<400> SEQUENCE: 12

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
        130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Glu Arg Ser Glu Leu Leu Leu Ser Glu Lys
            180                 185                 190
```

```
Val Val Asp Ala Arg Lys Ser Thr Trp His Val Phe Pro Val Ser Ser
            195                 200                 205

Ser Ile Gln Arg Leu Leu Asp Gln Gly Lys Ser Ser Leu Asp Val Arg
            210                 215                 220

Ile Ala Cys Glu Gln Cys Gln Glu Ser Gly Ala Ser Leu Val Leu Leu
225                 230                 235                 240

Gly Lys Lys Lys Lys Glu Glu Gly Glu Gly Lys Lys Gly
            245                 250                 255

Gly Gly Glu Gly Gly Ala Gly Ala Asp Glu Glu Lys Glu Gln Ser His
            260                 265                 270

Arg Pro Phe Leu Met Leu Gln Ala Arg Gln Ser Glu Asp His Pro His
            275                 280                 285
```

<210> SEQ ID NO 13
<211> LENGTH: 286
<212> TYPE: PRT
<213> ORGANISM: Artificial
<220> FEATURE:
<223> OTHER INFORMATION: Synthetic peptide

<400> SEQUENCE: 13

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ser Ala
            20                  25                  30

Pro Asp Cys Pro Ser Cys Ala Leu Ala Thr Leu Pro Lys Asp Gly Pro
            35                  40                  45

Asn Ser Gln Pro Glu Met Val Glu Ala Val Lys Lys His Ile Leu Asn
50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
            85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
            130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
            165                 170                 175

Gln Gln Gln Lys His Gly Glu Arg Ser Glu Leu Leu Leu Ser Glu Lys
            180                 185                 190

Val Val Asp Ala Arg Lys Ser Thr Trp His Ile Phe Pro Val Ser Ser
            195                 200                 205

Ser Ile Gln Arg Leu Leu Asp Gln Gly Lys Ser Ser Leu Asp Val Arg
            210                 215                 220

Ile Ala Cys Glu Gln Cys Gln Glu Ser Gly Ala Ser Leu Val Leu Leu
225                 230                 235                 240

Gly Lys Lys Lys Lys Glu Val Asp Gly Asp Lys Lys Asp
            245                 250                 255

Gly Ser Asp Gly Gly Leu Glu Glu Glu Lys Glu Gln Ser His Arg Pro
            260                 265                 270
```

Phe Leu Met Leu Gln Ala Arg Gln Ser Glu Asp His Pro His
            275                 280                 285

<210> SEQ ID NO 14
<211> LENGTH: 286
<212> TYPE: PRT
<213> ORGANISM: Artificial
<220> FEATURE:
<223> OTHER INFORMATION: Synthetic peptide

<400> SEQUENCE: 14

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ala Ala
            20                  25                  30

Pro Asp Cys Pro Ser Cys Ala Leu Ala Thr Leu Pro Lys Asp Gly Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Glu Arg Ser Glu Leu Leu Leu Ser Glu Lys
            180                 185                 190

Val Val Asp Ala Arg Lys Ser Thr Trp His Ile Phe Pro Val Ser Ser
        195                 200                 205

Ser Ile Gln Arg Leu Leu Asp Gln Gly Lys Ser Ser Leu Asp Val Arg
    210                 215                 220

Ile Ala Cys Glu Gln Cys Gln Glu Ser Gly Ala Ser Leu Val Leu Leu
225                 230                 235                 240

Gly Lys Lys Lys Lys Lys Glu Val Asp Gly Asp Gly Lys Lys Lys Asp
                245                 250                 255

Gly Ser Asp Gly Gly Leu Glu Glu Glu Lys Glu Gln Ser His Arg Pro
            260                 265                 270

Phe Leu Met Leu Gln Ala Arg Gln Ser Glu Asp His Pro His
        275                 280                 285

<210> SEQ ID NO 15
<211> LENGTH: 289
<212> TYPE: PRT
<213> ORGANISM: Artificial
<220> FEATURE:
<223> OTHER INFORMATION: Synthetic peptide

<400> SEQUENCE: 15

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Gly Glu Arg Ser Glu Leu Leu Leu Ser Glu
            180                 185                 190

Lys Val Val Asp Ala Arg Lys Ser Thr Trp His Val Phe Pro Val Ser
        195                 200                 205

Ser Ser Ile Gln Arg Leu Leu Asp Gln Gly Lys Ser Ser Leu Asp Val
    210                 215                 220

Arg Ile Ala Cys Glu Gln Cys Gln Glu Ser Gly Ala Ser Leu Val Leu
225                 230                 235                 240

Leu Gly Lys Lys Lys Lys Lys Glu Glu Glu Gly Glu Gly Lys Lys Lys
                245                 250                 255

Gly Gly Gly Glu Gly Gly Ala Gly Ala Asp Glu Glu Lys Glu Gln Ser
            260                 265                 270

His Arg Pro Phe Leu Met Leu Gln Ala Arg Gln Ser Glu Asp His Pro
        275                 280                 285

His

<210> SEQ ID NO 16
<211> LENGTH: 287
<212> TYPE: PRT
<213> ORGANISM: Artificial
<220> FEATURE:
<223> OTHER INFORMATION: Synthetic peptide

<400> SEQUENCE: 16

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ser Ala
            20                  25                  30

Pro Asp Cys Pro Ser Cys Ala Leu Ala Thr Leu Pro Lys Asp Gly Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
            130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Gly Glu Arg Ser Glu Leu Leu Leu Ser Glu
            180                 185                 190

Lys Val Val Asp Ala Arg Lys Ser Thr Trp His Ile Phe Pro Val Ser
            195                 200                 205

Ser Ser Ile Gln Arg Leu Leu Asp Gln Gly Lys Ser Ser Leu Asp Val
        210                 215                 220

Arg Ile Ala Cys Glu Gln Cys Gln Glu Ser Gly Ala Ser Leu Val Leu
225                 230                 235                 240

Leu Gly Lys Lys Lys Lys Lys Glu Val Asp Gly Asp Gly Lys Lys Lys
                245                 250                 255

Asp Gly Ser Asp Gly Gly Leu Glu Glu Glu Lys Glu Gln Ser His Arg
            260                 265                 270

Pro Phe Leu Met Leu Gln Ala Arg Gln Ser Glu Asp His Pro His
            275                 280                 285

<210> SEQ ID NO 17
<211> LENGTH: 287
<212> TYPE: PRT
<213> ORGANISM: Artificial
<220> FEATURE:
<223> OTHER INFORMATION: Synthetic peptide

<400> SEQUENCE: 17

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ala Ala
            20                  25                  30

Pro Asp Cys Pro Ser Cys Ala Leu Ala Thr Leu Pro Lys Asp Gly Pro
        35                  40                  45

Asn Ser Gln Pro Glu Met Val Glu Ala Val Lys Lys His Ile Leu Asn
50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
            130                 135                 140

Ser Asp Leu Ser Val Val Glu Arg Ala Glu Val Trp Leu Phe Leu Lys
145                 150                 155                 160

```
Val Pro Lys Ala Asn Arg Thr Arg Thr Lys Val Thr Ile Arg Leu Phe
            165                 170                 175

Gln Gln Gln Lys His Gly Gly Glu Arg Ser Glu Leu Leu Leu Ser Glu
            180                 185                 190

Lys Val Val Asp Ala Arg Lys Ser Thr Trp His Ile Phe Pro Val Ser
            195                 200                 205

Ser Ser Ile Gln Arg Leu Leu Asp Gln Gly Lys Ser Ser Leu Asp Val
            210                 215                 220

Arg Ile Ala Cys Glu Gln Cys Gln Glu Ser Gly Ala Ser Leu Val Leu
225                 230                 235                 240

Leu Gly Lys Lys Lys Lys Glu Val Asp Gly Asp Gly Lys Lys
            245                 250                 255

Asp Gly Ser Asp Gly Leu Glu Glu Glu Lys Glu Gln Ser His Arg
            260                 265                 270

Pro Phe Leu Met Leu Gln Ala Arg Gln Ser Glu Asp His Pro His
            275                 280                 285
```

<210> SEQ ID NO 18
<211> LENGTH: 290
<212> TYPE: PRT
<213> ORGANISM: Artificial
<220> FEATURE:
<223> OTHER INFORMATION: Synthetic peptide

<400> SEQUENCE: 18

```
Met Pro Leu Leu Trp Leu Arg Gly Phe Leu Leu Ala Ser Cys Trp Ile
1                   5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Gly Glu Arg Ser Glu Leu Leu Leu Ser
            180                 185                 190

Glu Lys Val Val Asp Ala Arg Lys Ser Thr Trp His Val Phe Pro Val
        195                 200                 205

Ser Ser Ser Ile Gln Arg Leu Leu Asp Gln Gly Lys Ser Ser Leu Asp
    210                 215                 220

Val Arg Ile Ala Cys Glu Gln Cys Gln Glu Ser Gly Ala Ser Leu Val
225                 230                 235                 240
```

```
Leu Leu Gly Lys Lys Lys Lys Glu Glu Gly Glu Gly Lys Lys
            245                 250                 255

Lys Gly Gly Gly Glu Gly Gly Ala Gly Ala Asp Glu Glu Lys Glu Gln
        260                 265                 270

Ser His Arg Pro Phe Leu Met Leu Gln Ala Arg Gln Ser Glu Asp His
    275                 280                 285

Pro His
    290

<210> SEQ ID NO 19
<211> LENGTH: 288
<212> TYPE: PRT
<213> ORGANISM: Artificial
<220> FEATURE:
<223> OTHER INFORMATION: Synthetic peptide

<400> SEQUENCE: 19

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ser Ala
            20                  25                  30

Pro Asp Cys Pro Ser Cys Ala Leu Ala Thr Leu Pro Lys Asp Gly Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Gly Gly Glu Arg Ser Glu Leu Leu Leu Ser
            180                 185                 190

Glu Lys Val Val Asp Ala Arg Lys Ser Thr Trp His Ile Phe Pro Val
        195                 200                 205

Ser Ser Ser Ile Gln Arg Leu Leu Asp Gln Gly Lys Ser Ser Leu Asp
    210                 215                 220

Val Arg Ile Ala Cys Glu Gln Cys Gln Glu Ser Gly Ala Ser Leu Val
225                 230                 235                 240

Leu Leu Gly Lys Lys Lys Lys Glu Val Asp Gly Asp Gly Lys Lys
                245                 250                 255

Lys Asp Gly Ser Asp Gly Gly Leu Glu Glu Glu Lys Glu Gln Ser His
        260                 265                 270

Arg Pro Phe Leu Met Leu Gln Ala Arg Gln Ser Glu Asp His Pro His
    275                 280                 285

<210> SEQ ID NO 20
<211> LENGTH: 288
```

```
<212> TYPE: PRT
<213> ORGANISM: Artificial
<220> FEATURE:
<223> OTHER INFORMATION: Synthetic peptide

<400> SEQUENCE: 20

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ala Ala
            20                  25                  30

Pro Asp Cys Pro Ser Cys Ala Leu Ala Thr Leu Pro Lys Asp Gly Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Gly Gly Glu Arg Ser Glu Leu Leu Leu Ser
            180                 185                 190

Glu Lys Val Val Asp Ala Arg Lys Ser Thr Trp His Ile Phe Pro Val
        195                 200                 205

Ser Ser Ser Ile Gln Arg Leu Leu Asp Gln Gly Lys Ser Ser Leu Asp
    210                 215                 220

Val Arg Ile Ala Cys Glu Gln Cys Gln Glu Ser Gly Ala Ser Leu Val
225                 230                 235                 240

Leu Leu Gly Lys Lys Lys Lys Lys Glu Val Asp Gly Asp Gly Lys Lys
                245                 250                 255

Lys Asp Gly Ser Asp Gly Gly Leu Glu Glu Glu Lys Glu Gln Ser His
            260                 265                 270

Arg Pro Phe Leu Met Leu Gln Ala Arg Gln Ser Glu Asp His Pro His
        275                 280                 285

<210> SEQ ID NO 21
<211> LENGTH: 408
<212> TYPE: PRT
<213> ORGANISM: Artificial
<220> FEATURE:
<223> OTHER INFORMATION: Synthetic peptide

<400> SEQUENCE: 21

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45
```

Asn Ser Gln Pro Glu Met Val Glu Ala Val Lys Lys His Ile Leu Asn
50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
                100                 105                 110

Met Asn Glu Leu Met Glu Gln Thr Ser Glu Ile Ile Thr Phe Ala Glu
                115                 120                 125

Ser Gly Thr Ala Arg Lys Thr Leu His Phe Glu Ile Ser Lys Glu Gly
                130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Glu Arg Ser Glu Leu Leu Ser Glu Lys Val
                180                 185                 190

Val Asp Ala Arg Lys Ser Thr Trp His Val Phe Pro Val Ser Ser Ser
                195                 200                 205

Ile Gln Arg Leu Leu Asp Gln Gly Lys Ser Ser Leu Asp Val Arg Ile
                210                 215                 220

Ala Cys Glu Gln Cys Gln Glu Ser Gly Ala Ser Leu Val Leu Leu Gly
225                 230                 235                 240

Lys Lys Lys Lys Lys Glu Glu Glu Gly Glu Gly Lys Lys Lys Gly Gly
                245                 250                 255

Gly Glu Gly Gly Ala Gly Ala Asp Glu Glu Lys Glu Gln Ser His Arg
                260                 265                 270

Pro Phe Leu Met Leu Gln Ala Arg Gln Ser Glu Asp His Pro His Arg
                275                 280                 285

Arg Arg Arg Arg Gly Leu Glu Cys Asp Gly Lys Val Asn Ile Cys Cys
                290                 295                 300

Lys Lys Gln Phe Phe Val Ser Phe Lys Asp Ile Gly Trp Asn Asp Trp
305                 310                 315                 320

Ile Ile Ala Pro Ser Gly Tyr His Ala Asn Tyr Cys Glu Gly Glu Cys
                325                 330                 335

Pro Ser His Ile Ala Gly Thr Ser Gly Ser Ser Leu Ser Phe His Ser
                340                 345                 350

Thr Val Ile Asn His Tyr Arg Met Arg Gly His Ser Pro Phe Ala Asn
                355                 360                 365

Leu Lys Ser Cys Cys Val Pro Thr Lys Leu Arg Pro Met Ser Met Leu
370                 375                 380

Tyr Tyr Asp Asp Gly Gln Asn Ile Ile Lys Lys Asp Ile Gln Asn Met
385                 390                 395                 400

Ile Val Glu Glu Cys Gly Cys Ser
                405

<210> SEQ ID NO 22
<211> LENGTH: 406
<212> TYPE: PRT
<213> ORGANISM: Artificial
<220> FEATURE:
<223> OTHER INFORMATION: Synthetic peptide

<400> SEQUENCE: 22

-continued

```
Met Pro Leu Leu Trp Leu Arg Gly Phe Leu Ala Ser Cys Trp Ile
1               5                   10                  15

Ile Val Arg Ser Ser Pro Thr Pro Gly Ser Glu Gly His Gly Ser Ala
            20                  25                  30

Pro Asp Cys Pro Ser Cys Ala Leu Ala Thr Leu Pro Lys Asp Gly Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Glu Arg Ser Glu Leu Leu Leu Ser Glu Lys Val
            180                 185                 190

Val Asp Ala Arg Lys Ser Thr Trp His Ile Phe Pro Val Ser Ser Ser
        195                 200                 205

Ile Gln Arg Leu Leu Asp Gln Gly Lys Ser Ser Leu Asp Val Arg Ile
        210                 215                 220

Ala Cys Glu Gln Cys Gln Glu Ser Gly Ala Ser Leu Val Leu Leu Gly
225                 230                 235                 240

Lys Lys Lys Lys Lys Glu Val Asp Gly Asp Gly Lys Lys Lys Asp Gly
                245                 250                 255

Ser Asp Gly Gly Leu Glu Glu Glu Lys Glu Gln Ser His Arg Pro Phe
            260                 265                 270

Leu Met Leu Gln Ala Arg Gln Ser Glu Asp His Pro His Arg Arg Arg
        275                 280                 285

Arg Arg Gly Leu Glu Cys Asp Gly Lys Val Asn Ile Cys Cys Lys Lys
    290                 295                 300

Gln Phe Phe Val Ser Phe Lys Asp Ile Gly Trp Asn Asp Trp Ile Ile
305                 310                 315                 320

Ala Pro Ser Gly Tyr His Ala Asn Tyr Cys Glu Gly Glu Cys Pro Ser
                325                 330                 335

His Ile Ala Gly Thr Ser Gly Ser Ser Leu Ser Phe His Ser Thr Val
            340                 345                 350

Ile Asn His Tyr Arg Met Arg Gly His Ser Pro Phe Ala Asn Leu Lys
        355                 360                 365

Ser Cys Cys Val Pro Thr Lys Leu Arg Pro Met Ser Met Leu Tyr Tyr
370                 375                 380

Asp Asp Gly Gln Asn Ile Ile Lys Lys Asp Ile Gln Asn Met Ile Val
385                 390                 395                 400

Glu Glu Cys Gly Cys Ser
                405
```

```
<210> SEQ ID NO 23
<211> LENGTH: 406
<212> TYPE: PRT
<213> ORGANISM: Artificial
<220> FEATURE:
<223> OTHER INFORMATION: Synthetic peptide

<400> SEQUENCE: 23

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ala Ala
                20                  25                  30

Pro Asp Cys Pro Ser Cys Ala Leu Ala Thr Leu Pro Lys Asp Gly Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Glu Arg Ser Glu Leu Leu Leu Ser Glu Lys Val
            180                 185                 190

Val Asp Ala Arg Lys Ser Thr Trp His Ile Phe Pro Val Ser Ser Ser
        195                 200                 205

Ile Gln Arg Leu Leu Asp Gln Gly Lys Ser Ser Leu Asp Val Arg Ile
    210                 215                 220

Ala Cys Glu Gln Cys Gln Glu Ser Gly Ala Ser Leu Val Leu Leu Gly
225                 230                 235                 240

Lys Lys Lys Lys Lys Glu Val Asp Gly Asp Gly Lys Lys Lys Asp Gly
                245                 250                 255

Ser Asp Gly Gly Leu Glu Glu Glu Lys Glu Gln Ser His Arg Pro Phe
            260                 265                 270

Leu Met Leu Gln Ala Arg Gln Ser Glu Asp His Pro His Arg Arg Arg
        275                 280                 285

Arg Arg Gly Leu Glu Cys Asp Gly Lys Val Asn Ile Cys Cys Lys Lys
    290                 295                 300

Gln Phe Phe Val Ser Phe Lys Asp Ile Gly Trp Asn Asp Trp Ile Ile
305                 310                 315                 320

Ala Pro Ser Gly Tyr His Ala Asn Tyr Cys Glu Gly Glu Cys Pro Ser
                325                 330                 335

His Ile Ala Gly Thr Ser Gly Ser Ser Leu Ser Phe His Ser Thr Val
            340                 345                 350

Ile Asn His Tyr Arg Met Arg Gly His Ser Pro Phe Ala Asn Leu Lys
        355                 360                 365
```

```
Ser Cys Cys Val Pro Thr Lys Leu Arg Pro Met Ser Met Leu Tyr Tyr
    370                 375                 380

Asp Asp Gly Gln Asn Ile Ile Lys Lys Asp Ile Gln Asn Met Ile Val
385                 390                 395                 400

Glu Glu Cys Gly Cys Ser
                    405

<210> SEQ ID NO 24
<211> LENGTH: 409
<212> TYPE: PRT
<213> ORGANISM: Artificial
<220> FEATURE:
<223> OTHER INFORMATION: Synthetic peptide

<400> SEQUENCE: 24

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Glu Arg Ser Glu Leu Leu Leu Ser Glu Lys
            180                 185                 190

Val Val Asp Ala Arg Lys Ser Thr Trp His Val Phe Pro Val Ser Ser
        195                 200                 205

Ser Ile Gln Arg Leu Leu Asp Gln Gly Lys Ser Ser Leu Asp Val Arg
210                 215                 220

Ile Ala Cys Glu Gln Cys Gln Glu Ser Gly Ala Ser Leu Val Leu Leu
225                 230                 235                 240

Gly Lys Lys Lys Lys Lys Glu Glu Glu Gly Glu Gly Lys Lys Lys Gly
                245                 250                 255

Gly Gly Glu Gly Gly Ala Gly Ala Asp Glu Glu Lys Glu Gln Ser His
            260                 265                 270

Arg Pro Phe Leu Met Leu Gln Ala Arg Gln Ser Glu Asp His Pro His
        275                 280                 285

Arg Arg Arg Arg Arg Gly Leu Glu Cys Asp Gly Lys Val Asn Ile Cys
        290                 295                 300

Cys Lys Lys Gln Phe Phe Val Ser Phe Lys Asp Ile Gly Trp Asn Asp
305                 310                 315                 320
```

```
Trp Ile Ile Ala Pro Ser Gly Tyr His Ala Asn Tyr Cys Glu Gly Glu
                325                 330                 335

Cys Pro Ser His Ile Ala Gly Thr Ser Gly Ser Ser Leu Ser Phe His
            340                 345                 350

Ser Thr Val Ile Asn His Tyr Arg Met Arg Gly His Ser Pro Phe Ala
        355                 360                 365

Asn Leu Lys Ser Cys Cys Val Pro Thr Lys Leu Arg Pro Met Ser Met
370                 375                 380

Leu Tyr Tyr Asp Asp Gly Gln Asn Ile Ile Lys Lys Asp Ile Gln Asn
385                 390                 395                 400

Met Ile Val Glu Glu Cys Gly Cys Ser
                405
```

<210> SEQ ID NO 25
<211> LENGTH: 407
<212> TYPE: PRT
<213> ORGANISM: Artificial
<220> FEATURE:
<223> OTHER INFORMATION: Synthetic peptide

<400> SEQUENCE: 25

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ser Ala
            20                  25                  30

Pro Asp Cys Pro Ser Cys Ala Leu Ala Thr Leu Pro Lys Asp Gly Pro
        35                  40                  45

Asn Ser Gln Pro Glu Met Val Glu Ala Val Lys Lys His Ile Leu Asn
50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Glu Arg Ser Glu Leu Leu Leu Ser Glu Lys
            180                 185                 190

Val Val Asp Ala Arg Lys Ser Thr Trp His Ile Phe Pro Val Ser Ser
        195                 200                 205

Ser Ile Gln Arg Leu Leu Asp Gln Gly Lys Ser Ser Leu Asp Val Arg
210                 215                 220

Ile Ala Cys Glu Gln Cys Gln Glu Ser Gly Ala Ser Leu Val Leu Leu
225                 230                 235                 240

Gly Lys Lys Lys Lys Lys Glu Val Asp Gly Asp Lys Lys Lys Lys Asp
                245                 250                 255

Gly Ser Asp Gly Gly Leu Glu Glu Glu Lys Glu Gln Ser His Arg Pro
            260                 265                 270
```

Phe Leu Met Leu Gln Ala Arg Gln Ser Glu Asp His Pro His Arg Arg
                275                 280                 285

Arg Arg Arg Gly Leu Glu Cys Asp Gly Lys Val Asn Ile Cys Cys Lys
    290                 295                 300

Lys Gln Phe Phe Val Ser Phe Lys Asp Ile Gly Trp Asn Asp Trp Ile
305                 310                 315                 320

Ile Ala Pro Ser Gly Tyr His Ala Asn Tyr Cys Gly Glu Cys Pro
                325                 330                 335

Ser His Ile Ala Gly Thr Ser Gly Ser Ser Leu Ser Phe His Ser Thr
                340                 345                 350

Val Ile Asn His Tyr Arg Met Arg Gly His Ser Pro Phe Ala Asn Leu
                355                 360                 365

Lys Ser Cys Cys Val Pro Thr Lys Leu Arg Pro Met Ser Met Leu Tyr
    370                 375                 380

Tyr Asp Asp Gly Gln Asn Ile Ile Lys Lys Asp Ile Gln Asn Met Ile
385                 390                 395                 400

Val Glu Glu Cys Gly Cys Ser
                405

<210> SEQ ID NO 26
<211> LENGTH: 407
<212> TYPE: PRT
<213> ORGANISM: Artificial
<220> FEATURE:
<223> OTHER INFORMATION: Synthetic peptide

<400> SEQUENCE: 26

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ala Ala
                20                  25                  30

Pro Asp Cys Pro Ser Cys Ala Leu Ala Thr Leu Pro Lys Asp Gly Pro
            35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
    115                 120                 125

Ser Gly Thr Ala Arg Lys Thr Leu His Phe Glu Ile Ser Lys Glu Gly
130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Glu Arg Ser Glu Leu Leu Leu Ser Glu Lys
            180                 185                 190

Val Val Asp Ala Arg Lys Ser Thr Trp His Ile Phe Pro Val Ser Ser
    195                 200                 205

Ser Ile Gln Arg Leu Leu Asp Gln Gly Lys Ser Ser Leu Asp Val Arg
210                 215                 220

```
Ile Ala Cys Glu Gln Cys Gln Glu Ser Gly Ala Ser Leu Val Leu Leu
225                 230                 235                 240

Gly Lys Lys Lys Lys Glu Val Asp Gly Asp Gly Lys Lys Lys Lys Asp
            245                 250                 255

Gly Ser Asp Gly Gly Leu Glu Glu Lys Glu Gln Ser His Arg Pro
                260                 265                 270

Phe Leu Met Leu Gln Ala Arg Gln Ser Glu Asp His Pro His Arg Arg
            275                 280                 285

Arg Arg Arg Gly Leu Glu Cys Asp Gly Lys Val Asn Ile Cys Cys Lys
        290                 295                 300

Lys Gln Phe Phe Val Ser Phe Lys Asp Ile Gly Trp Asn Asp Trp Ile
305                 310                 315                 320

Ile Ala Pro Ser Gly Tyr His Ala Asn Tyr Cys Glu Gly Glu Cys Pro
                325                 330                 335

Ser His Ile Ala Gly Thr Ser Gly Ser Ser Leu Ser Phe His Ser Thr
                340                 345                 350

Val Ile Asn His Tyr Arg Met Arg Gly His Ser Pro Phe Ala Asn Leu
            355                 360                 365

Lys Ser Cys Cys Val Pro Thr Lys Leu Arg Pro Met Ser Met Leu Tyr
370                 375                 380

Tyr Asp Asp Gly Gln Asn Ile Ile Lys Lys Asp Ile Gln Asn Met Ile
385                 390                 395                 400

Val Glu Glu Cys Gly Cys Ser
                405

<210> SEQ ID NO 27
<211> LENGTH: 410
<212> TYPE: PRT
<213> ORGANISM: Artificial
<220> FEATURE:
<223> OTHER INFORMATION: Synthetic peptide

<400> SEQUENCE: 27

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175
```

```
Gln Gln Gln Lys His Gly Gly Glu Arg Ser Glu Leu Leu Leu Ser Glu
            180                 185                 190

Lys Val Val Asp Ala Arg Lys Ser Thr Trp His Val Phe Pro Val Ser
        195                 200                 205

Ser Ser Ile Gln Arg Leu Leu Asp Gln Gly Lys Ser Ser Leu Asp Val
        210                 215                 220

Arg Ile Ala Cys Glu Gln Cys Gln Glu Ser Gly Ala Ser Leu Val Leu
225                 230                 235                 240

Leu Gly Lys Lys Lys Lys Glu Glu Gly Glu Gly Lys Lys Lys
            245                 250                 255

Gly Gly Gly Glu Gly Gly Ala Gly Ala Asp Glu Glu Lys Glu Gln Ser
            260                 265                 270

His Arg Pro Phe Leu Met Leu Gln Ala Arg Gln Ser Glu Asp His Pro
        275                 280                 285

His Arg Arg Arg Arg Gly Leu Glu Cys Asp Gly Lys Val Asn Ile
        290                 295                 300

Cys Cys Lys Lys Gln Phe Phe Val Ser Phe Lys Asp Ile Gly Trp Asn
305                 310                 315                 320

Asp Trp Ile Ile Ala Pro Ser Gly Tyr His Ala Asn Tyr Cys Glu Gly
                325                 330                 335

Glu Cys Pro Ser His Ile Ala Gly Thr Ser Gly Ser Ser Leu Ser Phe
            340                 345                 350

His Ser Thr Val Ile Asn His Tyr Arg Met Arg Gly His Ser Pro Phe
            355                 360                 365

Ala Asn Leu Lys Ser Cys Cys Val Pro Thr Lys Leu Arg Pro Met Ser
        370                 375                 380

Met Leu Tyr Tyr Asp Asp Gly Gln Asn Ile Ile Lys Lys Asp Ile Gln
385                 390                 395                 400

Asn Met Ile Val Glu Glu Cys Gly Cys Ser
                405                 410

<210> SEQ ID NO 28
<211> LENGTH: 408
<212> TYPE: PRT
<213> ORGANISM: Artificial
<220> FEATURE:
<223> OTHER INFORMATION: Synthetic peptide

<400> SEQUENCE: 28

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ser Ala
            20                  25                  30

Pro Asp Cys Pro Ser Cys Ala Leu Ala Thr Leu Pro Lys Asp Gly Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125
```

-continued

```
Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Gly Glu Arg Ser Glu Leu Leu Leu Ser Glu
                180                 185                 190

Lys Val Asp Ala Arg Lys Ser Thr Trp His Ile Phe Pro Val Ser
        195                 200                 205

Ser Ser Ile Gln Arg Leu Leu Asp Gln Gly Lys Ser Ser Leu Asp Val
210                 215                 220

Arg Ile Ala Cys Glu Gln Cys Gln Glu Ser Gly Ala Ser Leu Val Leu
225                 230                 235                 240

Leu Gly Lys Lys Lys Lys Glu Val Asp Gly Asp Gly Lys Lys Lys
                245                 250                 255

Asp Gly Ser Asp Gly Leu Glu Glu Glu Lys Glu Gln Ser His Arg
        260                 265                 270

Pro Phe Leu Met Leu Gln Ala Arg Gln Ser Glu Asp His Pro His Arg
    275                 280                 285

Arg Arg Arg Gly Leu Glu Cys Asp Gly Lys Val Asn Ile Cys Cys
290                 295                 300

Lys Lys Gln Phe Phe Val Ser Phe Lys Asp Ile Gly Trp Asn Asp Trp
305                 310                 315                 320

Ile Ile Ala Pro Ser Gly Tyr His Ala Asn Tyr Cys Glu Gly Glu Cys
                325                 330                 335

Pro Ser His Ile Ala Gly Thr Ser Gly Ser Ser Leu Ser Phe His Ser
                340                 345                 350

Thr Val Ile Asn His Tyr Arg Met Arg Gly His Ser Pro Phe Ala Asn
            355                 360                 365

Leu Lys Ser Cys Cys Val Pro Thr Lys Leu Arg Pro Met Ser Met Leu
370                 375                 380

Tyr Tyr Asp Asp Gly Gln Asn Ile Ile Lys Lys Asp Ile Gln Asn Met
385                 390                 395                 400

Ile Val Glu Glu Cys Gly Cys Ser
                405

<210> SEQ ID NO 29
<211> LENGTH: 408
<212> TYPE: PRT
<213> ORGANISM: Artificial
<220> FEATURE:
<223> OTHER INFORMATION: Synthetic peptide

<400> SEQUENCE: 29

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ala Ala
                20                  25                  30

Pro Asp Cys Pro Ser Cys Ala Leu Ala Thr Leu Pro Lys Asp Gly Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
65                  70                  75                  80
```

```
Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
            130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Gly Glu Arg Ser Glu Leu Leu Leu Ser Glu
            180                 185                 190

Lys Val Val Asp Ala Arg Lys Ser Thr Trp His Ile Phe Pro Val Ser
            195                 200                 205

Ser Ser Ile Gln Arg Leu Leu Asp Gln Gly Lys Ser Ser Leu Asp Val
            210                 215                 220

Arg Ile Ala Cys Glu Gln Cys Gln Glu Ser Gly Ala Ser Leu Val Leu
225                 230                 235                 240

Leu Gly Lys Lys Lys Lys Glu Val Asp Gly Asp Gly Lys Lys Lys
                245                 250                 255

Asp Gly Ser Asp Gly Gly Leu Glu Glu Glu Lys Glu Gln Ser His Arg
            260                 265                 270

Pro Phe Leu Met Leu Gln Ala Arg Gln Ser Glu Asp His Pro His Arg
            275                 280                 285

Arg Arg Arg Arg Gly Leu Glu Cys Asp Gly Lys Val Asn Ile Cys Cys
290                 295                 300

Lys Lys Gln Phe Phe Val Ser Phe Lys Asp Ile Gly Trp Asn Asp Trp
305                 310                 315                 320

Ile Ile Ala Pro Ser Gly Tyr His Ala Asn Tyr Cys Glu Gly Glu Cys
                325                 330                 335

Pro Ser His Ile Ala Gly Thr Ser Gly Ser Ser Leu Ser Phe His Ser
            340                 345                 350

Thr Val Ile Asn His Tyr Arg Met Arg Gly His Ser Pro Phe Ala Asn
            355                 360                 365

Leu Lys Ser Cys Cys Val Pro Thr Lys Leu Arg Pro Met Ser Met Leu
            370                 375                 380

Tyr Tyr Asp Asp Gly Gln Asn Ile Ile Lys Lys Asp Ile Gln Asn Met
385                 390                 395                 400

Ile Val Glu Glu Cys Gly Cys Ser
                405

<210> SEQ ID NO 30
<211> LENGTH: 411
<212> TYPE: PRT
<213> ORGANISM: Artificial
<220> FEATURE:
<223> OTHER INFORMATION: Synthetic peptide

<400> SEQUENCE: 30

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30
```

Pro Asp Cys Pro Ser Cys Ala Leu Ala Ala Leu Pro Lys Asp Val Pro
          35                  40                  45

Asn Ser Gln Pro Glu Met Val Glu Ala Val Lys Lys His Ile Leu Asn
 50                  55                  60

Met Leu His Leu Lys Lys Arg Pro Asp Val Thr Gln Pro Val Pro Lys
 65                  70                  75                  80

Ala Ala Leu Leu Asn Ala Ile Arg Lys Leu His Val Gly Lys Val Gly
                 85                  90                  95

Glu Asn Gly Tyr Val Glu Ile Glu Asp Asp Ile Gly Arg Arg Ala Glu
                100                 105                 110

Met Asn Glu Leu Met Glu Gln Thr Ser Glu Ile Ile Thr Phe Ala Glu
                115                 120                 125

Ser Gly Thr Ala Arg Lys Thr Leu His Phe Glu Ile Ser Lys Glu Gly
130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Gly Gly Glu Arg Ser Glu Leu Leu Leu Ser
                180                 185                 190

Glu Lys Val Val Asp Ala Arg Lys Ser Thr Trp His Val Phe Pro Val
            195                 200                 205

Ser Ser Ser Ile Gln Arg Leu Leu Asp Gln Gly Lys Ser Ser Leu Asp
            210                 215                 220

Val Arg Ile Ala Cys Glu Gln Cys Gln Glu Ser Gly Ala Ser Leu Val
225                 230                 235                 240

Leu Leu Gly Lys Lys Lys Lys Glu Glu Glu Gly Glu Gly Lys Lys
                245                 250                 255

Lys Gly Gly Gly Glu Gly Gly Ala Gly Ala Asp Glu Glu Lys Glu Gln
                260                 265                 270

Ser His Arg Pro Phe Leu Met Leu Gln Ala Arg Gln Ser Glu Asp His
            275                 280                 285

Pro His Arg Arg Arg Arg Gly Leu Glu Cys Asp Gly Lys Val Asn
            290                 295                 300

Ile Cys Cys Lys Lys Gln Phe Phe Val Ser Phe Lys Asp Ile Gly Trp
305                 310                 315                 320

Asn Asp Trp Ile Ile Ala Pro Ser Gly Tyr His Ala Asn Tyr Cys Glu
                325                 330                 335

Gly Glu Cys Pro Ser His Ile Ala Gly Thr Ser Gly Ser Ser Leu Ser
                340                 345                 350

Phe His Ser Thr Val Ile Asn His Tyr Arg Met Arg Gly His Ser Pro
            355                 360                 365

Phe Ala Asn Leu Lys Ser Cys Cys Val Pro Thr Lys Leu Arg Pro Met
370                 375                 380

Ser Met Leu Tyr Tyr Asp Asp Gly Gln Asn Ile Ile Lys Lys Asp Ile
385                 390                 395                 400

Gln Asn Met Ile Val Glu Glu Cys Gly Cys Ser
                405                 410

<210> SEQ ID NO 31
<211> LENGTH: 409
<212> TYPE: PRT
<213> ORGANISM: Artificial
<220> FEATURE:
<223> OTHER INFORMATION: Synthetic peptide

<400> SEQUENCE: 31

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Gly Ser Ala
            20                  25                  30

Pro Asp Cys Pro Ser Cys Ala Leu Ala Thr Leu Pro Lys Asp Gly Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Gly Gly Gly Glu Arg Ser Glu Leu Leu Leu Ser
            180                 185                 190

Glu Lys Val Val Asp Ala Arg Lys Ser Thr Trp His Ile Phe Pro Val
        195                 200                 205

Ser Ser Ser Ile Gln Arg Leu Leu Asp Gln Gly Lys Ser Ser Leu Asp
    210                 215                 220

Val Arg Ile Ala Cys Glu Gln Cys Gln Glu Ser Gly Ala Ser Leu Val
225                 230                 235                 240

Leu Leu Gly Lys Lys Lys Lys Lys Glu Val Asp Gly Asp Gly Lys Lys
                245                 250                 255

Lys Asp Gly Ser Asp Gly Gly Leu Glu Glu Glu Lys Glu Gln Ser His
            260                 265                 270

Arg Pro Phe Leu Met Leu Gln Ala Arg Gln Ser Glu Asp His Pro His
        275                 280                 285

Arg Arg Arg Arg Arg Gly Leu Glu Cys Asp Gly Lys Val Asn Ile Cys
290                 295                 300

Cys Lys Lys Gln Phe Phe Val Ser Phe Lys Asp Ile Gly Trp Asn Asp
305                 310                 315                 320

Trp Ile Ile Ala Pro Ser Gly Tyr His Ala Asn Tyr Cys Glu Gly Glu
                325                 330                 335

Cys Pro Ser His Ile Ala Gly Thr Ser Gly Ser Ser Leu Ser Phe His
            340                 345                 350

Ser Thr Val Ile Asn His Tyr Arg Met Arg Gly His Ser Pro Phe Ala
        355                 360                 365

Asn Leu Lys Ser Cys Cys Val Pro Thr Lys Leu Arg Pro Met Ser Met
    370                 375                 380

Leu Tyr Tyr Asp Asp Gly Gln Asn Ile Ile Lys Lys Asp Ile Gln Asn
385                 390                 395                 400

Met Ile Val Glu Glu Cys Gly Cys Ser
```

<210> SEQ ID NO 32
<211> LENGTH: 409
<212> TYPE: PRT
<213> ORGANISM: Artificial
<220> FEATURE:
<223> OTHER INFORMATION: Synthetic peptide

<400> SEQUENCE: 32

```
Met Pro Leu Leu Trp Leu Arg Gly Phe Leu Leu Ala Ser Cys Trp Ile
1               5                   10                  15
Ile Val Arg Ser Ser Pro Thr Pro Gly Ser Glu Gly His Gly Ala Ala
            20                  25                  30
Pro Asp Cys Pro Ser Cys Ala Leu Ala Thr Leu Pro Lys Asp Gly Pro
        35                  40                  45
Asn Ser Gln Pro Glu Met Val Glu Ala Val Lys Lys His Ile Leu Asn
    50                  55                  60
Met Leu His Leu Lys Lys Arg Pro Asp Val Thr Gln Pro Val Pro Lys
65                  70                  75                  80
Ala Ala Leu Leu Asn Ala Ile Arg Lys Leu His Val Gly Lys Val Gly
                85                  90                  95
Glu Asn Gly Tyr Val Glu Ile Glu Asp Asp Ile Gly Arg Arg Ala Glu
            100                 105                 110
Met Asn Glu Leu Met Glu Gln Thr Ser Glu Ile Ile Thr Phe Ala Glu
        115                 120                 125
Ser Gly Thr Ala Arg Lys Thr Leu His Phe Glu Ile Ser Lys Glu Gly
    130                 135                 140
Ser Asp Leu Ser Val Val Glu Arg Ala Glu Val Trp Leu Phe Leu Lys
145                 150                 155                 160
Val Pro Lys Ala Asn Arg Thr Arg Thr Lys Val Thr Ile Arg Leu Phe
                165                 170                 175
Gln Gln Gln Lys His Gly Gly Gly Glu Arg Ser Glu Leu Leu Leu Ser
            180                 185                 190
Glu Lys Val Val Asp Ala Arg Lys Ser Thr Trp His Ile Phe Pro Val
        195                 200                 205
Ser Ser Ser Ile Gln Arg Leu Leu Asp Gln Gly Lys Ser Ser Leu Asp
    210                 215                 220
Val Arg Ile Ala Cys Glu Gln Cys Gln Glu Ser Gly Ala Ser Leu Val
225                 230                 235                 240
Leu Leu Gly Lys Lys Lys Lys Lys Glu Val Asp Gly Asp Gly Lys Lys
                245                 250                 255
Lys Asp Gly Ser Asp Gly Gly Leu Glu Glu Glu Lys Glu Gln Ser His
            260                 265                 270
Arg Pro Phe Leu Met Leu Gln Ala Arg Gln Ser Glu Asp His Pro His
        275                 280                 285
Arg Arg Arg Arg Arg Gly Leu Glu Cys Asp Gly Lys Val Asn Ile Cys
    290                 295                 300
Cys Lys Lys Gln Phe Phe Val Ser Phe Lys Asp Ile Gly Trp Asn Asp
305                 310                 315                 320
Trp Ile Ile Ala Pro Ser Gly Tyr His Ala Asn Tyr Cys Glu Gly Glu
                325                 330                 335
Cys Pro Ser His Ile Ala Gly Thr Ser Gly Ser Ser Leu Ser Phe His
            340                 345                 350
Ser Thr Val Ile Asn His Tyr Arg Met Arg Gly His Ser Pro Phe Ala
```

```
                355                 360                 365
Asn Leu Lys Ser Cys Cys Val Pro Thr Lys Leu Arg Pro Met Ser Met
        370                 375                 380

Leu Tyr Tyr Asp Asp Gly Gln Asn Ile Ile Lys Lys Asp Ile Gln Asn
385                 390                 395                 400

Met Ile Val Glu Glu Cys Gly Cys Ser
                405
```

<210> SEQ ID NO 33
<211> LENGTH: 1167
<212> TYPE: DNA
<213> ORGANISM: Artificial
<220> FEATURE:
<223> OTHER INFORMATION: Synthetic DNA

<400> SEQUENCE: 33

```
agtcctactc ctggtagcga aggacattct gctgctccag attgtccttc ttgtgctctt    60
gctgctctgc ctaaggatgt gcctaattct cagcctgaga tggttgaggc tgtgaagaaa   120
cacatcctga acatgctgca cctgaagaaa aggcctgatg tgactcagcc tgttcctaag   180
gctgctttgc tgaacgctat taggaagctg cacgttggta aggtgggaga gaatggttac   240
gttgagatcg aggatgatat cggtagaagg gctgagatga acgagctgat ggaacagacc   300
tctgagatca tcaccttcgc tgagtctgga accgctagaa agactctgca cttcgagatc   360
agcaaagagg gtagcgatct gtctgttgtt gagagggctg aggtgtggct tttcttgaag   420
gtgccaaagg ctaataggac caggaccaag gtgaccatta ggcttttcca acagcagaag   480
cacgagagat ctgagttgct gctgtctgag aaggttgtgg atgctagaaa gtccacctgg   540
cacgttttcc ctgtgtcctc ttcaattcag aggctgctgg atcagggtaa gagcagcctt   600
gatgttagga ttgcttgcga gcagtgccaa gagtctggtg cttctcttgt gcttctgggt   660
aagaagaaaa agaaagagga gagggtgaaa ggtaagaaaa agggtggtgg tgaaggtggt   720
gctggtgctg atgaagagaa agagcagtct cacaggcctt tcttgatgct tcaggctagg   780
cagtctgagg atcaccctca cagaaggaga gaaggggtc  ttgagtgtga tggaaaggtg   840
aacatctgct gcaagaagca gttcttcgtt agcttcaagg atatcggttg gaacgattgg   900
atcattgctc aagcggtta ccacgctaat tactgtgagg gagagtgccc ttctcacatt   960
gctggtacta gcggaagctc tctgtctttc catagcaccg tgatcaacca ctacaggatg  1020
aggggacata gccctttcgc taacctgaag tcttgctgcg tgccaactaa gctgaggcct  1080
atgtctatgc tgtactacga tgatggtcag aacatcatca aaaaggatat ccagaacatg  1140
atcgtggaag agtgcggttg ctcttag                                     1167
```

<210> SEQ ID NO 34
<211> LENGTH: 1170
<212> TYPE: DNA
<213> ORGANISM: Artificial
<220> FEATURE:
<223> OTHER INFORMATION: Synthetic DNA

<400> SEQUENCE: 34

```
agtcctactc ctggtagcga aggacattct gctgctccag attgtccttc ttgtgctctt    60
gctgctctgc ctaaggatgt gcctaattct cagcctgaga tggttgaggc tgtgaagaaa   120
cacatcctga acatgctgca cctgaagaaa aggcctgatg tgactcagcc tgttcctaag   180
gctgctttgc tgaacgctat taggaagctg cacgttggta aggtgggaga gaatggttac   240
```

```
gttgagatcg aggatgatat cggtagaagg gctgagatga acgagctgat ggaacagacc    300
tctgagatca tcaccttcgc tgagtctgga accgctagaa agactctgca cttcgagatc    360
agcaaagagg gtagcgatct gtctgttgtt gagagggctg aggtgtggct tttcttgaag    420
gtgccaaagg ctaataggac caggaccaag gtgaccatta ggcttttcca acagcagaag    480
cacggtgaga gatctgagtt gctgctgtct gagaaggttg tggatgctag aaagtccacc    540
tggcacgttt tccctgtgtc ctcttcaatt cagaggctgc tggatcaggg taagagcagc    600
cttgatgtta ggattgcttg cgagcagtgc caagagtctg gtgcttctct tgtgcttctg    660
ggtaagaaga aaagaaaga ggaagaggga aaggtaagaa aaagggtgg tggtgaaggt    720 ggtgctggtg ctgatgaaga gaaagagcag tctcacaggc ctttcttgat gcttcaggct    780
aggcagtctg aggatcaccc tcacagaagg agaagaaggg gtcttgagtg tgatggaaag    840
gtgaacatct gctgcaagaa gcagttcttc gttagcttca aggatatcgg ttggaacgat    900
tggatcattg ctccaagcgg ttaccacgct aattactgtg agggagagtg cccttctcac    960
attgctggta ctagcggaag ctctctgtct ttccatagca ccgtgatcaa ccactacagg    1020
atgaggggac atagccctt cgctaacctg aagtcttgct gcgtgccaac taagctgagg    1080
cctatgtcta tgctgtacta cgatgatggt cagaacatca tcaaaaagga tatccagaac    1140
atgatcgtgg aagagtgcgg ttgctcttag                                     1170
```

<210> SEQ ID NO 35
<211> LENGTH: 1173
<212> TYPE: DNA
<213> ORGANISM: Artificial
<220> FEATURE:
<223> OTHER INFORMATION: Synthetic DNA

<400> SEQUENCE: 35

```
agtcctactc ctggtagcga aggacattct gctgctccag attgtccttc ttgtgctctt     60
gctgctctgc ctaaggatgt gcctaattct cagcctgaga tggttgaggc tgtgaagaaa    120
cacatcctga acatgctgca cctgaagaaa aggcctgatg tgactcagcc tgttcctaag    180
gctgctttgc tgaacgctat taggaagctg cacgttggta aggtgggaga gaatggttac    240
gttgagatcg aggatgatat cggtagaagg gctgagatga acgagctgat ggaacagacc    300
tctgagatca tcaccttcgc tgagtctgga accgctagaa agactctgca cttcgagatc    360
agcaaagagg gtagcgatct gtctgttgtt gagagggctg aggtgtggct tttcttgaag    420
gtgccaaagg ctaataggac caggaccaag gtgaccatta ggcttttcca acagcagaag    480
cacggtggtg agagatctga gttgctgctg tctgagaagg ttgtggatgc tagaaagtcc    540
acctggcacg ttttccctgt gtcctcttca attcagaggc tgctggatca gggtaagagc    600
agccttgatg ttaggattgc ttgcgagcag tgccaagagt ctggtgcttc tcttgtgctt    660
ctgggtaaga agaaaaagaa agaggaagag ggagaaggta gaaaaagggg tggtggtgaa    720
ggtggtgctg gtgctgatga agagaaagag cagtctcaca ggcctttctt gatgcttcag    780
gctaggcagt ctgaggatca ccctcacaga aggagaagaa ggggtcttga gtgtgatgga    840
aaggtgaaca tctgctgcaa gaagcagttc ttcgttagct tcaaggatat cggttggaac    900
gattggatca ttgctccaag cggttaccac gctaattact gtgagggaga gtgcccttct    960
cacattgctg gtactagcgg aagctctctg tctttccata gcaccgtgat caaccactac    1020
aggatgaggg gacatagccc tttcgctaac ctgaagtctt gctgcgtgcc aactaagctg    1080
aggcctatgt ctatgctgta ctacgatgat ggtcagaaca tcatcaaaaa ggatatccag    1140
```

<210> SEQ ID NO 36
<211> LENGTH: 1176
<212> TYPE: DNA
<213> ORGANISM: Artificial
<220> FEATURE:
<223> OTHER INFORMATION: Synthetic DNA

<400> SEQUENCE: 36

```
agtcctactc ctggtagcga aggacattct gctgctccag attgtccttc ttgtgctctt      60
gctgctctgc ctaaggatgt gcctaattct cagcctgaga tggttgaggc tgtgaagaaa     120
cacatcctga acatgctgca cctgaagaaa aggcctgatg tgactcagcc tgttcctaag     180
gctgctttgc tgaacgctat taggaagctg cacgttggta aggtgggaga gaatggttac     240
gttgagatcg aggatgatat cggtagaagg gctgagatga acgagctgat ggaacagacc     300
tctgagatca tcaccttcgc tgagtctgga accgctagaa agactctgca cttcgagatc     360
agcaaagagg gtagcgatct gtctgttgtt gagagggctg aggtgtggct tttcttgaag     420
gtgccaaagg ctaataggac caggaccaag gtgaccatta ggcttttcca acagcagaag     480
cacggtggtg gtgagagatc tgagttgctg ctgtctgaga aggttgtgga tgctagaaag     540
tccacctggc acgttttccc tgtgtcctct tcaattcaga ggctgctgga tcagggtaag     600
agcagccttg atgttaggat tgcttgcgag cagtgccaag agtctggtgc ttctcttgtg     660
cttctgggta agaagaaaaa gaaagaggaa gagggagaag gtaagaaaaa gggtggtggt     720
gaaggtggtg ctggtgctga tgaagagaaa gagcagtctc acaggccttt cttgatgctt     780
caggctaggc agtctgagga tcaccctcac agaaggagaa gaaggggtct tgagtgtgat     840
ggaaaggtga acatctgctg caagaagcag ttcttcgtta gcttcaagga tatcggttgg     900
aacgattgga tcattgctcc aagcggttac cacgctaatt actgtgaggg agagtgccct     960
tctcacattg ctggtactag cggaagctct ctgtctttcc atagcaccgt gatcaaccac    1020
tacaggatga ggggacatag ccctttcgct aacctgaagt cttgctgcgt gccaactaag    1080
ctgaggccta tgtctatgct gtactacgat gatggtcaga acatcatcaa aaaggatatc    1140
cagaacatga tcgtggaaga gtgcggttgc tcttag                              1176
```

<210> SEQ ID NO 37
<211> LENGTH: 432
<212> TYPE: PRT
<213> ORGANISM: Artificial
<220> FEATURE:
<223> OTHER INFORMATION: Synthetic peptide

<400> SEQUENCE: 37

```
His His His His His His Met Pro Leu Leu Trp Leu Arg Gly Phe Leu
  1               5                  10                  15

Leu Ala Ser Cys Trp Ile Ile Val Arg Ser Ser Pro Thr Pro Gly Ser
             20                  25                  30

Glu Gly His Ser Ala Ala Pro Asp Cys Pro Ser Cys Ala Leu Ala Ala
         35                  40                  45

Leu Pro Lys Asp Val Pro Asn Ser Gln Pro Glu Met Val Glu Ala Val
     50                  55                  60

Lys Lys His Ile Leu Asn Met Leu His Leu Lys Lys Arg Pro Asp Val
 65                  70                  75                  80

Thr Gln Pro Val Pro Lys Ala Ala Leu Leu Asn Ala Ile Arg Lys Leu
```

His Val Gly Lys Val Gly Glu Asn Gly Tyr Val Glu Ile Glu Asp Asp
            85                  90                  95                 100

Ile Gly Arg Arg Ala Glu Met Asn Glu Leu Met Glu Gln Thr Ser Glu
            115                 120                 125

Ile Ile Thr Phe Ala Glu Ser Gly Thr Ala Arg Lys Thr Leu His Phe
130                 135                 140

Glu Ile Ser Lys Glu Gly Ser Asp Leu Ser Val Val Glu Arg Ala Glu
145                 150                 155                 160

Val Trp Leu Phe Leu Lys Val Pro Lys Ala Asn Arg Thr Arg Thr Lys
                165                 170                 175

Val Thr Ile Arg Leu Phe Gln Gln Gln Lys His Pro Gln Gly Ser Leu
            180                 185                 190

Asp Thr Gly Glu Glu Ala Glu Glu Val Gly Leu Lys Gly Glu Arg Ser
            195                 200                 205

Glu Leu Leu Leu Ser Glu Lys Val Val Asp Ala Arg Lys Ser Thr Trp
210                 215                 220

His Val Phe Pro Val Ser Ser Ser Ile Gln Arg Leu Leu Asp Gln Gly
225                 230                 235                 240

Lys Ser Ser Leu Asp Val Arg Ile Ala Cys Glu Gln Cys Gln Glu Ser
                245                 250                 255

Gly Ala Ser Leu Val Leu Leu Gly Lys Lys Lys Lys Glu Glu Glu
            260                 265                 270

Gly Glu Gly Lys Lys Lys Gly Gly Glu Gly Gly Ala Gly Ala Asp
            275                 280                 285

Glu Glu Lys Glu Gln Ser His Arg Pro Phe Leu Met Leu Gln Ala Arg
290                 295                 300

Gln Ser Glu Asp His Pro His Arg Arg Arg Arg Gly Leu Glu Cys
305                 310                 315                 320

Asp Gly Lys Val Asn Ile Cys Cys Lys Lys Gln Phe Phe Val Ser Phe
                325                 330                 335

Lys Asp Ile Gly Trp Asn Asp Trp Ile Ile Ala Pro Ser Gly Tyr His
            340                 345                 350

Ala Asn Tyr Cys Glu Gly Glu Cys Pro Ser His Ile Ala Gly Thr Ser
            355                 360                 365

Gly Ser Ser Leu Ser Phe His Ser Thr Val Ile Asn His Tyr Arg Met
            370                 375                 380

Arg Gly His Ser Pro Phe Ala Asn Leu Lys Ser Cys Cys Val Pro Thr
385                 390                 395                 400

Lys Leu Arg Pro Met Ser Met Leu Tyr Tyr Asp Asp Gly Gln Asn Ile
                405                 410                 415

Ile Lys Lys Asp Ile Gln Asn Met Ile Val Glu Glu Cys Gly Cys Ser
            420                 425                 430

<210> SEQ ID NO 38
<211> LENGTH: 32
<212> TYPE: DNA
<213> ORGANISM: Artificial
<220> FEATURE:
<223> OTHER INFORMATION: Synthetic DNA

<400> SEQUENCE: 38
ccaacagcag aagcacgaga gatctgagtt gc                                   32

<210> SEQ ID NO 39

```
<211> LENGTH: 32
<212> TYPE: DNA
<213> ORGANISM: Artificial
<220> FEATURE:
<223> OTHER INFORMATION: Synthetic DNA

<400> SEQUENCE: 39
gcaactcaga tctctcgtgc ttctgctgtt gg                                    32
```

MODIFIED ACTIVIN A

TECHNICAL FIELD

The present invention relates to activin A comprising a modified amino acid sequence.

BACKGROUND ART

Activin A is a cytokine belonging to the TGFβ (transforming growth factor-β) superfamily. Activin A is a physiologically and industrially useful protein that is involved in development and differentiation as an erythroid differentiation factor and a mesoderm-inducing factor and regulates diverse functions in various cells.

Examples of known methods for producing protein include a production method by transiently expressing a protein of interest in a plant (Non Patent Literature 1: Sainsbury et al., Curr. Opin. Plant Biol., 19, 1-7, 2014) and a method of expressing a target protein in apoplast (Patent Literature 1: JP Laid-Open Publication No. 2005-501558).

However, it has been reported that when a target protein is expressed in a plant, the expressed target protein is degraded by an endogenous plant protease, causing the problem of a reduced yield (Non Patent Literature 2: Mandal MK. et al., Front Plant Sci., 7, 267, 2015). In particular, there are abundant proteases having various spectra (ranges) of specificities in apoplast (Non Patent Literature 3: Pillary P. et al., Bioengineered, 5: 1, 15-20, 2014). Furthermore, the site of the target protein recognized by a protease varies depending on the type of protein, and thus, it is difficult to predict the site. Known methods to address these problems include a method of changing protein localization by using a protein sorting signal and a method of coexpressing a protease inhibitor in a plant (Non Patent Literature 2 and Non Patent Literature 3).

Some conformations of activin A have been reported (Non Patent Literature 4: Wang X. et al., Nat. Commun. 2016 Jul. 4; 7: 12052). The structural information about the site recognized by a protease other than a proprotein convertase (Furin) is unknown.

CITATION LIST

Patent Literature

[Patent Literature 1]
  JP Laid-Open Publication No. 2005-501558

Non Patent Literature

[Non Patent Literature 1]
  Sainsbury et al., Curr. Opin. Plant Biol., 19, 1-7, 2014
[Non Patent Literature 2]
  Mandal MK. et al., Front Plant Sci., 7, 267, 2015
[Non Patent Literature 3]
  Pillary P. et al., Bioengineered, 5: 1, 15-20, 2014
[Non Patent Literature 4]
  Wang X. et al., Nat. Commun. 2016 Jul. 4; 7: 12052
[Non Patent Literature 5]
  Koretz K. et al., Histochemistry, 86: 5, 471-8, 1987

SUMMARY OF INVENTION

Technical Problem

As for activin A, conventionally known methods have not yet solved the problem of degradation by a protease other than a proprotein convertase (Furin) (hereinafter, may be simply referred to as "protease"). Accordingly, a novel activin A that is hard to be degraded by the above described protease (has resistance to degradation by the above described protease) is needed.

Solution to Problem

The present inventors conducted dedicated research to solve the above described problems and have found an unknown recognition site for proteases on activin A. Furthermore, the present inventors modified the amino acid sequence of a proregion of activin A, thereby successfully generating a modified activin A that is hard to be degraded by the protease, and thus, have accomplished the present invention.

Specifically, embodiments of the present invention are as follows:

(1) Activin A having resistance to degradation by a protease other than a proprotein convertase (Furin).

(2) The activin A according to the above described (1), wherein the protease other than a proprotein convertase (Furin) is an endogenous plant protease.

(3) The activin A according to the above described (1) or (2), wherein the activin A comprises a modified proregion.

(4) The activin A according to the above described (3), wherein the amino acid sequence of the modified proregion comprises an amino acid sequence in which at least one amino acid is deleted, substituted and/or added in an amino acid sequence from position 180 to 201 of an amino acid sequence set forth in any of SEQ ID NOs: 4 to 6.

(5) Activin A comprising a modified proregion, wherein the amino acid sequence of the modified proregion comprises an amino acid sequence in which at least one amino acid is deleted, substituted and/or added in the amino acid sequence from position 180 to 201 of an amino acid sequence set forth in any of SEQ ID NOs: 4 to 6.

(6) The activin A according to the above described (5), wherein the amino acid sequence of the modified proregion comprises any amino acid sequence selected from the following (a) to (d):

(a) an amino acid sequence in which an amino acid sequence from position 182 to 199 of an amino acid sequence set forth in any of SEQ ID NOs: 4 to 6 is deleted;

(b) an amino acid sequence in which an amino acid sequence from position 182 to 199 of an amino acid sequence set forth in any of SEQ ID NOs: 4 to 6 is substituted with a spacer sequence consisting of 1 to 10 amino acids;

(c) an amino acid sequence in which at least one of amino acids from position 182 to 199 of an amino acid sequence set forth in any of SEQ ID NOs: 4 to 6 is substituted with a different amino acid; and (d) an amino acid sequence in which an amino acid sequence from position 180 to 201 of an amino acid sequence set forth in any of SEQ ID NOs: 4 to 6 has at least one amino acid inserted therein.

(7) The activin A according to the above described (6), wherein the amino acid constituting the spacer sequence in the above (b) is at least one amino acid selected from glycine, alanine, and serine.

(8) The activin A according to the above described (6), wherein the different amino acid in the above (c) is one selected from alanine, serine, glycine, valine, leucine, and isoleucine.

(9) The activin A according to any of the above described (5) to (8), wherein the activin A has resistance to degradation by a protease other than a proprotein convertase (Furin). Herein, the protease other than a proprotein convertase (Furin) is, for example, an endogenous plant protease.

(10) The activin A according to the above described (5), wherein the amino acid sequence of the modified proregion comprises any of amino acid sequences selected from the following (e) to (g):
- (e) an amino acid sequence set forth in any of SEQ ID NOs: 9 to 20;
- (f) an amino acid sequence in which one or several amino acids are deleted, substituted or added in an amino acid sequence set forth in any of SEQ ID NOs: 9 to 20, and activin A comprising the amino acid sequence has resistance to degradation by a protease other than a proprotein convertase (Furin); and
- (g) an amino acid sequence having 80% or more homology with an amino acid sequence set forth in any of SEQ ID NOs: 9 to 20, and activin A comprising the amino acid sequence has resistance to degradation by a protease other than a proprotein convertase (Furin).

(11) A polynucleotide encoding the activin A according to any of the above described (1) to (10).

(12) A vector comprising the polynucleotide according to the above described (11).

(13) A transformant expressing the activin A according to any of the above described (1) to (10).

(14) The transformant according to the above described (13), wherein the transformant is a plant.

(15) The transformant according to the above described (14), wherein the transformant expresses the activin A in apoplast.

(16) A method for producing activin A, comprising the step of recovering the activin A expressed in the transformant according to any of the above described (13) to (15).

(17) A method for producing activin A, comprising the following steps:
- (a) recovering the activin A expressed in the transformant according to any of the above described (13) to (15); and
- (b) treating the obtained activin A with a proprotein convertase.

Effects of Invention

The modified activin A of the present invention allows for improving the yield of activin A in producing the activin A in the presence of the protease other than a proprotein convertase (Furin) (for example, in planta), compared to a wild type activin A that is not modified.

BRIEF DESCRIPTION OF DRAWINGS

FIG. 1 is a schematic figure showing the structure of a human activin A.

FIG. 2 is an image demonstrating that degradation of a modified activin A by proteases was suppressed.

DESCRIPTION OF EMBODIMENTS

Hereinbelow, the present invention will be described in detail. The following embodiment is illustrated to describe the present invention and is not intended to limit the present invention to this embodiment. The present invention may be carried out in various modes without departing from the spirits of the present invention. This specification also encompasses the contents described in the specification and drawings of the Japanese patent application (Japanese Patent Application No. 2018-214630) filed on Nov. 15, 2018, to which the present application claims priority.

1. Summary

Activin A is a cytokine belonging to the TGFβ superfamily. Activin A is a physiologically and industrially useful protein that is involved in development and differentiation as an erythroid differentiation factor and a mesoderm-inducing factor and regulates diverse functions in various cells.

An exemplary method for producing a target protein is a method of producing the protein by transiently expressing the same in a plant. However, it has been reported that when a target protein is expressed in a plant, the expressed target protein is degraded by a protease other than a proprotein convertase (Furin) (for example, an endogenous plant protease), causing the problem of a reduced yield. In particular, the abundance of endogenous proteases in apoplast is a major obstacle to expression of the target protein in the apoplast. Furthermore, the site of the target protein recognized by a protease varies depending on the type of protein, and thus, it is difficult to predict the site.

To address these problems, a method of changing protein localization by using a protein sorting signal and a method of coexpressing a protease inhibitor in a plant have been used in the conventional art. However, the problem of degradation by a protease still remains unsolved for activin A.

Under such circumstances, the present inventors have found an unknown recognition site for proteases on activin A; and modified the amino acid sequence of a proregion (also referred to herein as "prodomain") of activin A, thereby successfully generating a modified activin A that is hard to be degraded by a protease other than a proprotein convertase (Furin) (has resistance to degradation by the protease). Thus, the present inventors have accomplished the present invention. The present invention provides a modified activin A that is hard to be degraded by the protease, by modifying the amino acid sequence of the proregion of activin A. The present inventors have found that activin A becomes hard to be degraded by the protease by modifying an amino acid sequence of a proregion of the activin A without modifying an amino acid sequence of a mature region of the activin A that is physiologically active.

The modified activin A of the present invention allows for improving the yield of activin A in producing the activin A in the presence of the protease other than a proprotein convertase (Furin) (for example, in planta), compared to an unmodified wild type activin A. In this respect, the modified activin A of the present invention is highly useful.

2. Activin A and Modified Form Thereof

Activin A is a cytokine belonging to the TGFβ (transforming growth factor-β) superfamily. Activin A is a protein that is involved in development and differentiation as an erythroid differentiation factor and a mesoderm-inducing factor and regulates diverse functions in various cells.

The present invention provides activin A that is hard to be degraded by a protease other than a proprotein convertase (Furin) (has resistance to degradation by the above protease), by modifying the amino acid sequence of a proregion of activin A. Such activin A allows for improving the yield of activin A in producing the same in the presence of the protease, compared to a wild type activin A that is unmodified.

In the present invention, "activin A" refers to both or either one of pro-activin A and mature activin A. As the term "activin A" is used in the present invention, activin A may be a mixture of pro-activin A and mature activin A or may be either protein. Pro-activin A is a precursor of mature activin A and is a protein comprising a proregion, a recognition region for a proprotein converting enzyme, and a mature region (FIG. 1).

In the present invention, examples of the amino acid sequence of pro-activin A include, but not limited to, an amino acid sequence set forth in SEQ ID NO: 1 (human), SEQ ID NO: 2 (mouse), and SEQ ID NO: 3 (rat). In the present invention, examples of the amino acid sequence of the proregion include, but not limited to, an amino acid sequence set forth in SEQ ID NO: 4 (human), SEQ ID NO: 5 (mouse), and SEQ ID NO: 6 (rat). The amino acid sequence of the recognition region for a proprotein converting enzyme is an amino acid sequence set forth in SEQ ID NO: 7, and the amino acid sequence of the mature region (mature activin A) is an amino acid sequence set forth in SEQ ID NO: 8. Those skilled in the art can readily obtain these amino acid sequences and conformational information from known databases such as GenBank and UniProt Protein Data Bank (PDB). For example, human pro-activin A has GenBank accession number NP_002183.1 and PDB accession number 5HLLY.

Mature activin A is a protein comprising a mature region, the protein being generated when pro-activin A is cleaved by a proprotein converting enzyme (Furin). Mature activin A is a homodimer formed by linking 116-amino acid residue βA chains by a disulfide bond.

In the present invention, the type of animals from which activin A is derived is not limited. Examples of the animals include a human, a mouse, a rat, a guinea pig, a rabbit, a cat, a dog, a pig, a monkey, and a cow. Preferably, the animal is a human. The amino acid sequences of the mature region of activin A have 100% homology among humans, mice, rats, cats, pigs, and cows.

The present invention provides activin A that has resistance to degradation by a protease other than a proprotein convertase (Furin). In the present invention, a "protease other than a proprotein convertase (Furin)" is not limited, as long as the protease has the activity of degrading (for example, cleaving) activin A. The protease in the present invention may be an endogenous protease comprised in a transformant of a host such as a plant, a non-human mammal and a cell derived therefrom, a bacterium, a yeast, and a fungus, or may be an exogenous protease, which is found outside the transformant. The protease is preferably an endogenous plant protease or an exogenous plant protease, and more preferably an endogenous plant protease. Specifically, there are abundant proteases having various spectra (ranges) of specificities in a plant body (for example, apoplast) (Pillary P. et al., Bioengineered, 5: 1, 15-20, 2014), and thus, the endogenous plant protease is not limited, as long as the protease has the activity of degrading activin A.

Those skilled in the art can determine whether a specific protease has the activity of degrading activin A by using a known method such as SDS-PAGE and Western blotting.

In the present invention, the phrase "have resistance to degradation by a protease other than a proprotein convertase (Furin)" means that, in particular, when pro-activin A was expressed in a transformant, extracted, and purified as necessary and then the resulting protein was analyzed, the percentage of pro-activin A content relative to the total resulting protein is usually 70% or more, preferably 80% or more, and more preferably 84% or more. This phrase does not necessarily mean that the percentage of the pro-activin A content has to be 100% (not necessarily mean that degradation has to be suppressed by 100%). The amount or percentage of pro-activin A content can be measured by Western blotting as described in Examples. Thus, those skilled in the art can determine whether the modified activin A has resistance to degradation by a protease other than a proprotein convertase (Furin) by measuring the amount or percentage of the pro-activin A content relative to the total protein by Western blotting.

In the present invention, "protease other than a proprotein convertase (Furin)" may be expressed as "protease (excluding a proprotein convertase (Furin)."

One embodiment of the present invention is activin A comprising a modified proregion. A modified proregion is a proregion in which a sequence expected as a loop region is modified, and is preferably a proregion in which, among loop regions in the proregion, at least one sequence expected as a loop region has been deleted. Herein, the loop region is a part having a loop structure, and more specifically, a part from position 182 to 199 of an amino acid sequence set forth in any of SEQ ID NOs: 4 to 6.

In the present invention, the amino acid sequence of the modified proregion comprises an amino acid sequence in which at least one amino acid is deleted, substituted and/or added in an amino acid sequence from position 180 to 201 of an amino acid sequence set forth in any of SEQ ID NOs: 4 to 6 (activin A comprising a modified proregion is also referred to herein as "modified activin A").

The present invention also provides activin A comprising a modified proregion, wherein the amino acid sequence of the modified proregion comprises an amino acid sequence in which at least one amino acid is deleted, substituted and/or added in an amino acid sequence from position 180 to 201 of an amino acid sequence set forth in any of SEQ ID NOs: 4 to 6, and the activin A has resistance to degradation by a protease other than a proprotein convertase (Furin).

Examples of the amino acid sequence of the modified proregion include, but not limited to, the following amino acid sequences (a) to (d):

(a) an amino acid sequence in which an amino acid sequence from position 182 to 199 of an amino acid sequence set forth in any of SEQ ID NOs: 4 to 6 is deleted;

(b) an amino acid sequence in which an amino acid sequence from position 182 to 199 of an amino acid sequence set forth in any of SEQ ID NOs: 4 to 6 is substituted with a spacer sequence consisting of 1 to 10 amino acids;

(c) an amino acid sequence in which at least one of amino acids from position 182 to 199 of an amino acid sequence set forth in any of SEQ ID NOs: 4 to 6 is substituted with a different amino acid; and (d) an amino acid sequence in which an amino acid sequence from position 180 to 201 of an amino acid sequence set forth in any of SEQ ID NOs: 4 to 6 has at least one amino acid inserted therein.

Furthermore, examples of the amino acid sequence of the modified proregion include, but not limited to, amino acid sequences which are the following amino acid sequences (a) to (d) and wherein activin A comprising the amino acid sequence has resistance to degradation by a protease other than a proprotein convertase (Furin), (a) an amino acid sequence in which an amino acid sequence from position 182 to 199 of an amino acid sequence set forth in any of SEQ ID NOs: 4 to 6 is deleted;

(b) an amino acid sequence in which an amino acid sequence from position 182 to 199 of an amino acid sequence set forth in any of SEQ ID NOs: 4 to 6 is substituted with a spacer sequence consisting of 1 to 10 amino acids;

(c) an amino acid sequence in which at least one of amino acids from position 182 to 199 of an amino acid sequence set forth in any of SEQ ID NOs: 4 to 6 is substituted with a different amino acid; and (d) an amino acid sequence in which an amino acid sequence from position 180 to 201 of an amino acid sequence set forth in any of SEQ ID NOs: 4 to 6 has at least one amino acid inserted therein.

The above described amino acid sequence (a) is the amino acid sequence set forth in any of SEQ ID NO: 9 (human), SEQ ID NO: 10 (mouse), and SEQ ID NO: 11 (rat).

In the amino acid sequence (b), a "spacer sequence" is an amino acid sequence consisting of 1 to 10 amino acids. The amino acid constituting the spacer sequence is at least one selected from glycine, alanine, and serine. Specifically, the spacer sequence may be an amino acid sequence composed of only one type of amino acid, such as only glycine or only alanine; or may be an amino acid sequence composed of two or more types of amino acids, for example: glycine and alanine; glycine and alanine and leucine. The number of amino acids in the spacer sequence is 1 to 10, preferably 1 to 5, more preferably 1 to 4, and even more preferably 1 to 3. More specifically, examples of the spacer sequence include -G-, -GG-, -GGG-, and -GGGG-. In the present invention, when a spacer consists of one amino acid residue, "spacer sequence" may also be referred to as "spacer residue."

Those skilled in the art can search for the type and number of amino acid candidates as well as amino acid sequence candidates that constitute the spacer sequence by using molecular visualization software described below. Furthermore, in the present invention, a substructure can be inserted instead of the spacer sequence, provided that the substructure is registered in PDB, has ends whose relative coordinates correspond to the coordinates of an insertion site on activin A, can form a peptide bond, and does not cause a steric hindrance after insertion.

Examples of the above described amino acid sequence (b) include, but not limited to, an amino acid sequence set forth in any of SEQ ID NO: 12 (human), SEQ ID NO: 13 (mouse), and SEQ ID NO: 14 (rat) that comprises one glycine as the spacer sequence; an amino acid sequence set forth in any of SEQ ID NO: 15 (human), SEQ ID NO: 16 (mouse), and SEQ ID NO: 17 (rat) that comprises two glycines as the spacer sequence; and an amino acid sequence set forth in any of SEQ ID NO: 18 (human), SEQ ID NO: 19 (mouse), and SEQ ID NO: 20 (rat) that comprises three glycines as the spacer sequence.

In the above amino acid sequence (c), a "different amino acid" is not limited as long as the amino acid does not cause a steric hindrance in activin A. Examples thereof include alanine, serine, glycine, valine, leucine, and isoleucine.

In the above amino acid sequence (d), the amino acid to be inserted is not limited as long as the amino acid does not cause a steric hindrance in activin A. Examples thereof include alanine, serine, glycine, valine, leucine, and isoleucine.

In the present invention, in addition to the above described amino acid sequence set forth in any of SEQ ID NOs: 9 to 20, the following amino acid sequences can be used as an amino acid sequence of the modified proregion:

(f) an amino acid sequence in which one or several amino acids are deleted, substituted or added in an amino acid sequence set forth in any of SEQ ID NOs: 9 to 20, and activin A comprising the amino acid sequence has resistance to degradation by a protease other than a proprotein convertase (Furin); and (g) an amino acid sequence having 80% or more homology with an amino acid sequence set forth in any of SEQ ID NOs: 9 to 20, and activin A comprising the amino acid sequence has resistance to degradation by a protease other than a proprotein convertase (Furin).

In the above amino acid sequence (f), examples of an amino acid sequence in which one or several amino acids are deleted, substituted or added in set forth in any of SEQ ID NOs: 9 to 20 include the following amino acid sequences:

(i) an amino acid sequence in which 1 to 10 (for example, 1 to 5, preferably 1 to 3, more preferably 1 to 2, and even more preferably 1) amino acids of an amino acid sequence set forth in any of SEQ ID NOs: 9 to 20 is deleted;

(ii) an amino acid sequence in which 1 to 10 (for example, 1 to 5, preferably 1 to 3, more preferably 1 to 2, and even more preferably 1) amino acids of an amino acid sequence set forth in any of SEQ ID NOs: 9 to 20 is substituted with a different amino acid;

(iii) an amino acid sequence in which 1 to 10 (for example, 1 to 5, preferably 1 to 3, more preferably 1 to 2, and even more preferably 1) amino acids are added to an amino acid sequence set forth in any of SEQ ID NOs: 9 to 20; and (iv) an amino acid sequence mutated by a combination of the above described (i) to (iii).

In the above amino acid sequence (g), examples of the amino acid sequence having 80% or more homology with an amino acid sequence set forth in any of SEQ ID NOs: 9 to 20 include an amino acid sequence having 80% or more, 90% or more, 95% or more, 98% or more, or 99% or more homology with an amino acid sequence set forth in any of SEQ ID NOs: 9 to 20.

Those skilled in the art can readily examine homology among amino acid sequences by using a known database such as FASTA or BLAST.

In the present invention, "resistance to degradation by a protease other than a proprotein convertase (Furin)" means the property that makes activin A hard to be degraded by a protease other than a proprotein convertase (Furin). Furthermore, as described above, the phrase "have resistance to degradation by a protease other than a proprotein convertase (Furin)" in the present invention means that, in particular, when pro-activin A was expressed in a transformant, extracted, and purified as necessary and then the resulting protein was analyzed, the percentage of pro-activin A content relative to the total resulting protein is usually 70% or more, preferably 80% or more, and more preferably 84% or more. This phrase does not necessarily mean that the percentage of the pro-activin A content has to be 100% (not necessarily mean that degradation has to be suppressed by 100%). Those skill in the art can determine whether a modified activin A has resistance to degradation by a protease other than a proprotein convertase (Furin) by measuring the amount or percentage of the pro-activin A content relative to the total protein by Western blotting, as described in Examples.

The present invention also provides activin A comprising a modified proregion, wherein the amino acid sequence of the modified proregion comprises an amino acid sequence in which at least one amino acid has been deleted, substituted and/or added in an amino acid sequence from position 180 to 201 of an amino acid sequence set forth in any of SEQ ID NOs: 4 to 6, and wherein the activin A has the activity of inducing differentiation into an erythroblast when cleaved by a proprotein converting enzyme.

Examples of the amino acid sequence of the modified proregion include, but not limited to, the below described amino acid sequences (a) to (g). Examples of the activin A comprising a modified proregion include, but not limited to, the activin A comprising any of the below described amino acid sequences (a) to (g) and having the activity of inducing differentiation into an erythroblast when cleaved by a proprotein converting enzyme.

(a) an amino acid sequence in which an amino acid sequence from position 182 to 199 of an amino acid sequence set forth in any of SEQ ID NOs: 4 to 6 is deleted;

(b) an amino acid sequence in which an amino acid sequence from position 182 to 199 of an amino acid sequence set forth in any of SEQ ID NOs: 4 to 6 is substituted with a spacer sequence consisting of 1 to 10 amino acids;

(c) an amino acid sequence in which at least one of amino acids from position 182 to 199 of an amino acid sequence set forth in any of SEQ ID NOs: 4 to 6 is substituted with a different amino acid;

(d) an amino acid sequence in which an amino acid sequence from position 180 to 201 of an amino acid sequence set forth in any of SEQ ID NOs: 4 to 6 has at least one amino acid inserted therein;

(e) an amino acid sequence set forth in any of SEQ ID NOs: 9 to 20;

(f) an amino acid sequence in which one or several amino acids are deleted, substituted or added in an amino acid sequence set forth in any of SEQ ID NOs: 9 to 20; and (g) an amino acid sequence having 80% or more homology with an amino acid sequence set forth in any of SEQ ID NOs: 9 to 20.

In the present invention, "has the activity of inducing differentiation into an erythroblast when cleaved by a proprotein converting enzyme" means that activin A resulting from cleavage by a proprotein converting enzyme (a mixture of pro-activin A and mature activin A or mature activin A) has the activity of inducing differentiation of any erythroblastic cultured cell (for example, a F5-5 cell and a K562 cell) into an erythroblast.

The activity of inducing differentiation into an erythroblast can be evaluated by a known method. An exemplary method comprises adding a test polypeptide (test activin A) to the culture solution of erythroblastic cultured cells, staining the cells after cultivation with aminoethylcarbazole (AEC) or the like, and measuring the $ED_{50}$ value of the test activin A to determine the differentiation rate.

In the present invention, examples of the amino acid sequence of activin A comprising a modified proregion include, but not limited to, amino acid sequences of activin A comprising each of the amino acid sequences set forth in SEQ ID NOs: 9 to 20 (amino acid sequences set forth in SEQ ID NOs: 21 to 32).

The conformation of activin A with modification (deletion, substitution, addition, or a combination thereof) can be analyzed and simulated by using molecular visualization software that displays the structure of a protein in a 3D image based on data in PDB or the like. Examples of such software include Chimera and PyMOL. For example, the above amino acid sequence (a), in which the amino acid sequence from position 182 to 199 has been deleted and no spacer sequence has been inserted, can be subjected to simulation based on an in silico analysis using Chimera to find out whether a steric hindrance occurs. For the above amino acid sequence (b), the above software can be used to search for the type and number of amino acids or amino acid sequence candidates that constitute the spacer sequence. Similarly, the above amino acid sequences (c) and (d) can be subjected to simulation to find out whether a steric hindrance or the like occurs when substitution or insertion by a different amino acid was introduced in the amino acid sequence from position 182 to 199. Thus, those skilled in the art can select appropriately an amino acid residue that causes no steric hindrance when being deleted, substituted and/or added in activin A by using such molecular visualization software.

Furthermore, the chemical property or physical property of amino acids (polar/non-polar, acidic/basic, hydrophilic/hydrophobic, side chain size, and the like) is known. Those skilled in the art can appropriately select an amino acid to be deleted, substituted, and/or added on the basis of these properties. Substitution between amino acids that have similar structures or properties is predicted to be hard to substantially inhibit the biological activity of a polypeptide.

1) Polar amino acids: lysine, arginine, histidine, aspartic acid, glutamic acid, serine, threonine, asparagine, glutamine, tyrosine, and cysteine;
2) Nonpolar amino acids: glycine, alanine, valine, leucine, isoleucine, phenylalanine, tryptophan, methionine, and proline;
3) Acidic amino acids: aspartic acid and glutamic acid;
4) Basic amino acids: lysine, arginine, and histidine;
5) Neutral amino acids: glycine, alanine, valine, leucine, isoleucine, phenylalanine, tyrosine, tryptophan, serine, threonine, asparagine, glutamine, methionine, cysteine, and proline;
6) Aliphatic amino acids: glycine, alanine, valine, leucine, and isoleucine;
7) Aromatic amino acids: phenylalanine, tyrosine, and tryptophan;
8) Amino acids having a hydroxyl group: serine and threonine;
9) Amino acids having an amido group: asparagine and glutamine;
10) Sulfur-containing amino acids: methionine and cysteine;
11) Hydrophobic amino acids: glycine, alanine, valine, leucine, isoleucine, phenylalanine, tyrosine, tryptophan, methionine, cysteine, and proline (it is noted that glycine, tyrosine, tryptophan, and cysteine may be classified as hydrophilic amino acids);
12) Hydrophilic amino acids: lysine, arginine, histidine, aspartic acid, glutamic acid, asparagine, glutamine, serine, and threonine.

3. Polynucleotide, Vector, and Transformant (1) Polynucleotide

The nucleotide sequence of a polynucleotide of the present invention is not limited as long as the sequence is DNA or RNA encoding a modified activin A of the present invention. Those skilled in the art can optimize codons for the polynucleotide depending on the type of host in which activin A is expressed. This optimization can improve the amount of the modified activin A expressed in the host. Examples of the polynucleotide encoding the modified activin A of the present invention include, but not limited to, a polynucleotide comprising or consisting of a nucleotide sequence set forth in any of SEQ ID NOs: 33 to 36 (all thereof are human nucleotide sequences).

In addition to the polynucleotide comprising or consisting of a nucleotide sequence set forth in any of SEQ ID NOs: 33 to 36, a polynucleotide described below can be used as the polynucleotide of the present invention. Such a polynucleotide is a polynucleotide that hybridizes with a polynucleotide consisting of a nucleotide sequence complementary to a nucleotide sequence set forth in any of SEQ ID NOs: 33 to 36 under stringent conditions and encodes activin A having resistance to degradation by a protease other than a proprotein convertase (Furin). In the present invention, a "stringent condition" may be either a low stringency condition, a moderate stringency condition, or a high stringency condition. A "low stringency condition" is, for example, the following condition: 5×SSC, 5×Denhardt's solution, 0.5% SDS, 50% formamide, and 32° C. A "medium stringency condition" is, for example, the following condition: 5×SSC, 5×Denhardt's solution, 0.5% SDS, 50% formamide, and 42° C. A "high stringency condition" is, for example, the following condition: 5×SSC, 5×Denhardt's solution, 0.5% SDS, 50% formamide, and 50° C. For a detailed procedure of a hybridization method, one can refer to "Molecular Cloning, A Laboratory Manual (4th edition)" (Cold Spring Harbor Laboratory Press (2012)), and the like.

As the polynucleotide of the present invention, a polynucleotide that has 50% or more, 60% or more, 70% or more, 80% or more, 90% or more, 95% or more, 98% or more, or 99% or more homology with the nucleotide sequence set forth in any of SEQ ID NOs: 33 to 36, and encodes activin A having resistance to degradation by a protease other than a proprotein convertase (Furin) can also be used.

Methods for introducing a mutation into a polynucleotide are known. For example, those skilled in the art can introduce a mutation into the polynucleotide of the present invention by using a known method including a site-directed mutagenesis strategy such as the Kunkel method and the Gapped duplex method, the overlap extension PCR method and the QuikChange method. The amino acid sequence of activin A can be modified by introducing a mutation into the polynucleotide of the present invention.

In the present invention, an affinity tag can be added to activin A for affinity-purifying activin A. Examples of usable affinity tags include, but not limited to, a histidine tag (an amino acid sequence consisting of contiguous histidine residues), a GST tag, a FLAG tag, and a c-myc tag. Methods for adding a histidine tag are known and those skilled in the art can readily add a histidine tag to the N-terminus of the activin A of the present invention by using a known method. One example of the amino acid sequences of activin A with a histidine tag added to the N-terminus thereof is set forth in SEQ ID NO: 37.

In the present invention, a signal sequence can also be added to activin A. Examples of the signal sequence include a KDEL signal. Methods for adding a signal sequence are known. A sequence optimized for expression thereof in a plant cell can be used.

(2) Vector

In the present invention, a "vector" is not limited as long as the vector comprises the polynucleotide of the present invention described in the above (1). For example, a plasmid vector, a viral vector, an *Agrobacterium* bacterium, or the like can be used. When a plant is used as a host, for example, a plant viral vector, an *Agrobacterium* bacterium, or the like can be used as the vector. More specifically, for example, a TMV-based vector, a PVX-based vector, a CPMV-based vector, a CMV-based vector, a PPV-based vector, an AIMV-based vector, a ZYMV-based vector, or the like can be used. The vector used in the present invention may be either a vector for transient expression or a vector for constitutive expression. Those skilled in the art can appropriately select a vector to be used depending on the type of host into which the vector is introduced and the purpose.

In the vector of the present invention, an additional sequence may be linked to the polynucleotide of the present invention, as desired. Examples of the additional sequence include a cis element such as an enhancer, a splicing signal, a poly(A) addition signal, a ribosome binding sequence (SD sequence), a selective marker gene, and a reporter gene. Examples of the selective marker gene include a dihydrofolate reductase gene, an ampicillin-resistant gene, and a neomycin-resistant gene. Examples of the reporter gene include genes for green fluorescent protein (GFP) or variants thereof (fluorescent proteins such as EGFP, BFP, and YFP), luciferase, alkaline phosphatase, and LacZ.

(3) Transformant

In the present invention, a transformant can be obtained by introducing the vector described in the above (2) into a host. In the present invention, a "transformant" is a non-human transformant. In the present invention, a "host" is an organism into which the vector of the present invention is introduced and in which a modified activin A of interest is expressed. The host is not limited as long as the host expresses the modified activin A of the present invention. For example, a plant, a non-human mammal and a cell derived therefrom, a bacterium, a yeast, a fungus, or the like can be used, and a plant is preferred. Examples of the plant include a *Nicotiana* plant, a moss plant (for example, *Physcomitrella patens* (*P. patens*)), a potato (for example, *S. tuberosum*), a gramineous plant (for example, *O. sativa*), a cruciferous plant, and lettuce; and a *Nicotiana* plant is preferred. Examples of the *Nicotiana* plant include, but not limited to, *Nicotiana benthamiana* (*N. benthamiana*), *Nicotiana tabacum* (*N. tabacum*), and *Nicotiana excelsior* (*N. excelsior*). Examples of the non-human mammal include, but not limited to, a mouse, a rat, a guinea pig, a rabbit, a cat, a dog, a pig, a monkey, and a cow, and a cell derived therefrom. Examples of the bacterium include, but not limited to, *E. coli*.

Introduction of a vector into a host can be performed by using a known method. Examples of the known gene introduction method include a method using a viral vector, an agroinfection method, a calcium phosphate method, a microinjection method, a particle gun method, a DEAE-dextran method, electroporation, and a cationic lipid-mediated method. When the host is a plant, the method using a viral plant vector and the agroinfection method are preferred. The vectors that can be used in these methods are as described in the above (2) as "a vector when a plant is used as a host."

In the present invention, when a plant is used as a host, the plant is cultivated before transformation. A method for cultivating plants is as described below.

First, seeds are sown on a seedling tray supplemented with a fertilizer, and the plant after sowing is grown for several days in an artificial climate chamber with a controlled light cycle. When a liquid fertilizer is used as the fertilizer, a urethane mat for hydroponics can be impregnated with the liquid fertilizer, and then placed in the seedling tray.

Then, the grown plant body is transplanted to a panel for cultivation (first period), the panel after transplantation is placed in the artificial climate chamber, and cultivation is performed for several days by, for example, a deep flow technique (DFT system).

Subsequently, the plant body is taken out from the panel for cultivation (first period) and planted on a panel for cultivation (second period). The panel for cultivation (second period) after transplantation is placed in the artificial climate chamber and cultivation is performed for several days by the DFT system to obtain the plant body.

In the above described method, a liquid fertilizer can be used as the fertilizer, but the fertilizer is not limited thereto. When a liquid fertilizer is used, the urethane mat for hydroponics can be impregnated with the liquid fertilizer, and then placed in the seedling tray.

In the present invention, liquid fertilizers are not limited, and commercially available liquid fertilizers can be used in appropriate combinations. The liquid fertilizer can be dissolved in dechlorinated water. Furthermore, the electric conductivity and pH of the liquid fertilizer can be adjusted before use. Those skilled in the art can adjust these by a known method.

In the present invention, examples of the environmental condition include, but not limited to, a condition with a temperature of 10 to 40° C. (for example, 28° C.), a relative humidity of 60 to 80%, a $CO_2$ concentration of 300 to 5000 ppm (for example, 400 ppm or 500 ppm), and the number of days of cultivation for the first period of 0 to 35 days (for example, 9 days) and that for the second period of 0 to 35 days (for example, 7 days). Those skilled in the art can adjust these parameters as appropriate depending on, for example, the growth status of the plant.

In the present invention, as hydroponic techniques, the deep flow technique (DFT system) and a nutrient film technique (NFT system) can be mainly used.

As described above, when the host is a plant, the method using a plant viral vector and the agroinfection method can be used. These methods are well known to those skilled in the art. By way of example, a brief description of the agroinfection method is as follows.

First, the vector of the present invention described in the above (2) is introduced into an *Agrobacterium* bacterium by electroporation, thereby transforming the *Agrobacterium* bacterium. Examples of *Agrobacterium* bacterium that can be used in the present invention include, but not limited to, the GV3101 strain, the LBA4404 strain, the EHA101 strain, the EHA105 strain, and the AGL1 strain.

Then, plant leaves or the like are infected with the transformed *Agrobacterium* bacterium. Examples of methods for infecting a plant with an *Agrobacterium* bacterium include a vacuum infiltration method, a syringe infiltration method, a leaf disc method, and a foliar application method. An exemplary procedure for using the vacuum infiltration method is as follows. First, the cultivated plant is turned upside down and immersed in the bacterial suspension of *Agrobacterium* bacteria in a beaker such that all the leaves are completely immersed in the suspension. Subsequently, the beaker is placed in a vacuum desiccator and allowed to stand for several minutes (for example, one minute) under reduced pressure. Then, the valve is fully opened to restore pressure. After completing pressure restoration, the plant is returned to an upright position and planted in the artificial climate chamber. After infection, the plant is cultivated for 1 to 14 days (for example, 6 days) in the artificial climate chamber by, for example, the DFT system. The environmental condition is similar to that described above, and those skilled in the art can adjust these parameters as appropriate depending on, for example, the growth status of the plant.

In this way, a transformant of the plant can be generated. In infecting a plant with the *Agrobacterium* bacterium, the plant may be coinfected with multiple types of *Agrobacterium* bacteria, each comprising a different vector. In this case, *Agrobacterium* bacteria comprising a vector other than the vector of the present invention may be used in combination. Examples of such vector include a vector comprising a signal peptide of a barley α-amylase or a rice α-amylase, and a PhiC31 integrase expression vector.

Transformants from other hosts can also be generated readily by those skilled in the art by a known method described in, for example, "Molecular Cloning, A Laboratory Manual (4th edition)" (Cold Spring Harbor Laboratory Press (2012)).

4. Method for Producing Activin A

In the present invention, activin A can be produced by recovering activin A from the transformant of the present invention described in the above section 3. Furthermore, in the method of the present invention, a mature region of activin A in which a proregion is removed (mature activin A) can be obtained by purifying the recovered activin A (pro-activin A) and treating the purified pro-activin A with a proprotein convertase (for example, Furin).

The type of transformant used in the method for producing activin A is not limited. By way of example, when the transformant is a plant, the method for producing activin A is as described below.

First, leaves are collected from the transformed plant body that was cultivated for 1 to 14 days (for example, 6 days) after infection with *Agrobacterium* bacterium, and activin A (pro-activin A) is extracted by using an extraction buffer. The quantity of leaves of the plant body to be collected depends on the type of plant body. The leaves can be frozen and stored at −80° C. before extraction. Examples of the extraction buffer include, but not limited to, phosphate buffer, Tris buffer, and acetate buffer. The pH is usually adjusted to a range between pH 2 and 11, including the range in which the above described buffers work properly.

Next, activin A comprised in the extract is purified. Purification can be performed by using conventional methods alone or in appropriate combinations. The conventional methods are, for example, aqueous two-phase partition, ammonium sulfate fractionation, affinity chromatography, ion exchange chromatography, gel filtration chromatography, hydrophobic chromatography, or reverse-phase chromatography.

Conventional methods can be used to confirm that the resulting purified substance is the target protein, activin A. Examples of the conventional methods include SDS-polyacrylamide gel electrophoresis, N-terminal amino acid sequence analysis, Western blotting, enzyme immunoassay (ELISA), and mass spectrometry.

In this way, purified activin A (pro-activin A) can be obtained.

Furthermore, the mature region of activin A in which a proregion is removed (mature activin A) can be obtained by treating the purified pro-activin A with a proprotein convertase (Furin). A mixture of the proregion and the mature activin A may also be used for experiments.

The activity of the obtained mature activin A (or the mixture of the proregion and the mature activin A) can be evaluated, for example by cultivating a F5-5 cell line (Friend erythroblastic leukemia cell line) in a culture medium supplemented with the mature activin A, then staining the cells with AEC (aminoethylcarbazole), and measuring the $ED_{50}$ value (indicating the concentration of mature activin A at which the differentiation rate is 50%) of the mature activin A for the differentiation rate.

5. Composition Comprising Activin A

The present invention can provide a composition comprising a modified activin A of the present invention. The composition of the present invention may comprise known additives such as saline, buffer, and an excipient, in addition to the modified activin A.

Hereinbelow, the present invention will be described in detail by way of examples, but the present invention is not limited to these examples.

Example 1

1. Designing Modified Activin A

In this example, a sequence from which a specific sequence of a proregion was removed was designed.

When pro-activin A, which was transiently expressed by a plant, was extracted and then subjected to Western blotting, a plurality of unexpected degradation products was found. Thus, a plurality of sequences to induce site-specific mutations was designed and mutations were induced by using QuikChange (Agilent Technologies, Inc.). The mutated protein was overexpressed and examined in the same way as the above described original sequence. As a result, it was confirmed that the degradation was reduced in more than one sequences. The sequences were a sequence from which Pro182-Gly199 was removed. The Pro182-Gly192 was predicted to be a loop region of the prodomain. PDB 5HLY was used to adjust the dihedral angle between H181 and E200 and these residues were linked by a peptide bond. As a result, it was found not to cause a steric hindrance, and thus, this protein was designed as Mut3-1. Furthermore, an appropriate linker sequence was introduced between the above H181 and E200. A sequence into which (Gly)n (n=1 to 4) was introduced was designed to perform expression screening. Based on SuperLooper (Hypertext Transfer Protocol (HTTP)//bioinf-applied.charite.de/superlooper/description.php), the above linkers (Gly)n (n=2 or 3) that have the relative position coordinates of the residues, H181 and E200 for linker introduction were extracted from the registered PDB structure information (3DZM, 2VK3, and 5AA5 having GG, and 4GNO having GGG). Thus, sequences of Mut3-2 (n=1), Mut3-3 (n=2), and Mut3-4 (n=3) were designed.

Example 2

Production of Modified Activin A

On the basis of the information of the modified activin A designed in Example 1, the modified activin A was produced by a below described method.

1. Preparation of Vector

A vector for expressing pro-activin A in which a histidine tag (HHHHHH) was added to the N-terminus thereof was generated as described below. A gene encoding pro-activin A in which a histidine tag was added to the N-terminus thereof was inserted into a Bsa I site of a tobacco mosaic virus (TMV) 3'-provector (pICH31070, NOMAD Bioscience GmbH) by Golden Gate cloning method (Engler et al., 2008), thereby generating a pN-His-Pro-activin.

Next, a TMV 3'-provector that expresses a gene encoding a modified pro-activin A was generated as described below. PCR was carried out by using QuikChange Lightning Kit (Agilent Technologies, Inc.) with the pN-His-Pro-activin as a template and the following primers for mutation introduction, thereby generating a pMut3-1.

(SEQ ID NO: 38)
5'-CCAACAGCAGAAGCACGAGAGATCTGAGTTGC-3'

(SEQ ID NO: 39)
5'-GCAACTCAGATCTCTCGTGCTTCTGCTGTTGG-3

2. Generation of Transformant (1) Cultivation of Host Plant

In this example, *Nicotiana benthamiana*, which is a *Nicotiana* plant, was used as a host plant.

(1-1) Sowing

A urethane mat for hydroponics (Ematsu Kasei; (W)587.5 mm×(D)282 mm×(H)28 mm; 12×2 blocks; hole diameter ($\phi$): 9 mm) was impregnated with a liquid fertilizer for sowing (0.78 g/L Otsuka House No. S1 (Otsuka AgriTechno Co., Ltd.) and 0.25 g/L Otsuka House No. 2 (Otsuka AgriTechno Co., Ltd.); pH 5.0) and placed in a seedling tray ((W)600 mm×(D)300 mm×(H)300 mm). Then, seeds of *Nicotiana benthamiana* were sown on the mat.

(1-2) Raising Seedlings

The plant after sowing was grown in an artificial climate chamber (NC-410HC) (Nippon Medical & Chemical Instruments Co., Ltd.) at a room temperature of 28° C. with a light cycle of 16 hours of light and 8 hours of darkness for 12 days.

(1-3) Cultivation (First Period)

The urethane mat used for raising seedlings was divided into each block and transplanted to a panel for cultivation (first period) ((W)600 mm×(D)300 mm, 30 holes). The panel for cultivation (first period) after transplantation was placed in the artificial climate chamber (LH-410SP) (Nippon Medical & Chemical Instruments Co., Ltd.) and cultivation was performed for 9 days by a deep flow technique (DFT system). The environmental conditions and the liquid fertilizer conditions were controlled as follows.

«Environmental Conditions»

Temperature: 28° C.

Relative humidity: 40 to 60%

$CO_2$ concentration: 400 ppm

Lighting: average photosynthetic photon flux density (PPFD): 140 $\mu mol \cdot m^{-2} \cdot sec^{-1}$, 24 hours continuous lighting, a three band fluorescent lamp "Rupika Line" (Mitsubishi Electric Corporation)

«Liquid Fertilizer Conditions»

Fertilizer liquid A (150 g/L Otsuka House No. S1 and 2.5 g/L Otsuka House No. 5 (Otsuka AgriTechno Co., Ltd.)) and fertilizer liquid B (100 g/L Otsuka House No. 2) were dissolved individually in dechlorinated water and these solutions were mixed in equal proportions. The resulting mixture was used as the liquid fertilizer. A pH adjuster "Down" (Otsuka AgriTechno Co., Ltd.) and 4% aqueous KOH solution were used to adjust pH. The electrical conductivity (EC) and the pH of the liquid fertilizer were adjusted to an EC of 2.3 mS/cm and pH 6.0, respectively, by using "Easy Fertilizer Controller RAKU-RAKU 3" (CEM Corporation).

(1-4) Cultivation (Second Period)

The plant body was taken out from the panel for cultivation (first period) and planted on a panel for cultivation (second period) ((W)600 mm×(D)300 mm, 6 holes). The panel for cultivation (second period) after transplantation was placed in the artificial climate chamber (LH-410SP) (Nippon Medical & Chemical Instruments Co., Ltd.) and cultivation was performed for 7 days by the DFT system (for 28 days after sowing). Environmental conditions were controlled as described below.

«Environmental Conditions»
 Temperature: 28° C.
 Relative humidity: 60 to 80%
 $CO_2$ concentration: 500 ppm
 Lighting: average photosynthetic photon flux density (PPFD): 140 μmol·m$^{-2}$·sec$^{-1}$, 24 hours continuous lighting, a three band fluorescent lamp "Rupika Line" (Mitsubishi Electric Corporation)

(2) Generation of Transformant (2-1) Infection by Vacuum Infiltration

The vectors of the present invention generated in the above "1." were individually introduced into an *Agrobacterium* GV3101 strain by electroporation. Then, agroinfiltration was used to coinfect *Nicotiana benthamiana* with each of the obtained GV3101 strains: a GV3101 strain carrying a 5'-provector comprising a signal peptide of rice α-amylase (pICH20155, NOMAD Bioscience GmbH) and a GV3101 strain carrying a PhiC31 integrase expression vector (pICH14011, NOMAD Bioscience GmbH).

Specifically, the *Nicotiana benthamiana* obtained on Day 28 after sowing in the above section "2.(1)" was turned upside down and immersed in the bacterial suspension of *Agrobacterium* bacteria in a beaker such that all the leaves were completely submerged in the suspension.

Subsequently, the beaker was placed in a vacuum desiccator (FV-3P) (Tokyo Glass Kikai Co., Ltd.) and allowed to stand for one minute under reduced pressure at −0.09 MPa. Then, the valve was fully opened to restore pressure.

After completing pressure restoration, the plant was returned to an upright position and planted in the artificial climate chamber (LH-410SP) (Nippon Medical & Chemical Instruments Co., Ltd.).

(2-2) Cultivation of Infected Leaves (Expression Step)

Cultivation after infection was performed by using the artificial climate chamber (LH-410SP) (Nippon Medical & Chemical Instruments Co., Ltd.). Cultivation was performed for six days by the DFT system. Environmental conditions were controlled as described below.

«Environmental Conditions»
 Temperature: 28° C.
 Relative humidity: 60 to 80%
 $CO_2$ concentration: 500 ppm
 Lighting: average photosynthetic photon flux density (PPFD): 140 μmol·m$^{-2}$·sec$^{-1}$, 24 hours continuous lighting, a three band fluorescent lamp "Rupika Line" (Mitsubishi Electric Corporation)

3. Production of Modified Pro-activin A (1) Extraction

Tobacco leaves were harvested from the transformed *Nicotiana benthamiana* six days after infection. The leaves were frozen and stored at −80° C. until extraction.

A buffer comprising 0.1 M sodium phosphate, 0.5 M arginine, and 5 mM sodium sulfite, pH 8.0 (or a phosphate buffer) was used as an extraction buffer.

(2) Purification (2-1) Purification by Ammonium Sulfate Fraction

Ammonium sulfate was added to the supernatant collected by the above described method to produce a 35% saturated ammonium sulfate solution. After stirring the mixture at room temperature for one hour, the mixture was centrifuged at 15,000×g for 15 minutes at room temperature to collect the supernatant of 35% ammonium sulfate fractionation. Subsequently, ammonium sulfate was added thereto to produce a 60% saturated ammonium sulfate solution and stirred at room temperature for one hour. This solution was centrifuged at 15,000×g for 15 minutes to collect precipitates of the 60 to 90% ammonium sulfate fractionation.

(2-2) Purification by Affinity Chromatography

To 50 g of precipitates of the 60 to 90% ammonium sulfate fractionation from activin A-expressing tobacco leaves, 10 mL of equilibration solution for histidine (His)-tag affinity purification (20 mM HEPES, 150 mM NaCl, 10% (w/v) glycerol, pH 8.0) was added, and the precipitate was dissolved. This solution was passed through a HisTrap HP 1 mL column (GE Healthcare) equilibrated with the equilibration solution for His-tag affinity purification at a speed to achieve retention time of 3 minutes. Then, the column was washed with a washing solution for His-tag affinity purification (20 mM HEPES, 150 mM NaCl, 20 mM imidazole, 10% (w/v) glycerol, pH 8.0). Lastly, an elution solution for His-tag affinity purification (20 mM HEPES, 150 mM NaCl, 200 mM imidazole, 10% (w/v) glycerol, pH 8.0) was passed through the column and the elution peak was collected to obtain a modified pro-activin A.

4. Production of Mature Activin A

A proprotein convertase (Furin) was added to the modified pro-activin A obtained by the above described method (Mut3-1, Mut3-2, Mut3-3, and Mut3-4 (comprising the amino acid sequences of SEQ ID NOs: 9, 12, 15, and 18, respectively)) under conditions of 25 mM Tris-HCl, pH 8.0, 10% glycerol, and 1 mM $CaCl_2$ to obtain a mature activin A.

In this example, activin A in which an amino acid sequence of a proregion was modified (a modified pro-activin A and a mature activin A) was successfully produced.

Example 3

1. Functional Analysis of Modified Pro-activin A

The purified modified pro-activin A obtained in "3. Production of Modified Pro-activin A" of Example 2 was analyzed by Western blotting to determine how a plant endogenous protease degraded the protein. Specifically, Penta-His Antibody HRP Conjugate (QIAGEN) was used as an antibody and the samples comprising each modified pro-activin A were subjected to Western blotting. LumiGLO Reagent and Peroxide (Cell Signaling Technology, Inc.) was used as a luminescent reagent and was detected by ImageQuant LAS 500 (GE Healthcare). The obtained Western blotting image is shown in FIG. 2. Wild-type Activin A (N-His-Activin A in the figure) (SEQ ID NO: 37) was used as a control. Densitometric analysis was also performed by using analysis software ImageJ and the results are shown in Table 1. In Table 1, "other polypeptides" are peptides resulting from degradation of the expressed proteins by the plant endogenous protease.

TABLE 1

| Expressed protein | N-His-Activin A | Mut3-1 | Mut3-2 | Mut3-3 | Mut3-4 |
|---|---|---|---|---|---|
| Pro-activin A | 63% | 87% | 84% | 86% | 89% |
| Other polypeptides | 37% | 13% | 16% | 14% | 11% |

The results indicate that degradation of the modified activin A of the present invention by the plant endogenous protease was significantly suppressed compared to the non-modified activin A (N-His-Activin A, which is the wild type activin A) (FIG. 2).

This example demonstrated that the modified activin A of the present invention had the property of being hard to be degraded by a protease (resistance to degradation by a protease). This example also demonstrated that the modified activin A of the present invention was extremely useful in producing activin A in the presence of a protease, which is present in a host for expression, in a purification step, in a reagent and/or culture medium to be used, and the like. The reason for this is that the modified activin A of the present invention allows for improving the amount of expression thereof and/or the yield thereof compared to the nonmodified activin A.

2. Evaluation of Activity of Mature Activin A

The activity of the mature activin A obtained in "4. Production of Mature Activin A" of Example 2 was evaluated. F5-5 cells cultured in an incubator (37° C., 5% $CO_2$) were seeded in a 96 well plate and cultured in the incubator after adding each mature activin A. Then, the differentiation rate of the cells was determined by staining the cells with AEC (aminoethylcarbazole, Tokyo Chemical Industry Co., Ltd.), according to the method described in Non Patent Literature 5 (Koretz K. et al., Histochemistry, 86: 5, 471-8, 1987). Table 2 shows the $ED_{50}$ value of the mature activin A derived from the wild type activin A (N-His-Activin A) and the mature activin A derived from the modified activin A (Mut3-1 to Mut3-4).

TABLE 2

| Expressed protein | $ED_{50}$ ng/ml |
|---|---|
| N-His-Activin A | <5 |
| Mut3-1 | <5 |
| Mut3-2 | <5 |
| Mut3-3 | <5 |
| Mut3-4 | <5 |

As shown in Table 2, the $ED_{50}$ values of the mature activin A derived from the modified activin A ("Mut3-1" to "Mut3-4" in Table 2) were all less than 5 ng/mL, which were comparable to those of the mature activin A derived from the wild-type activin A ("N-His-Activin A" in Table 2).

These results indicated that the mature activin A obtained by treating the modified activin A with Furin had an ability to induce differentiation of the F5-5 cell into an erythroblast, with the same level of the wild-type activin A, and thus, it had an activity as mature activin A with same level of the activity of the wild-type activin A.

INDUSTRIAL APPLICABILITY

Use of the modified activin A of the present invention allows for improving the yield of activin A in producing the same in the presence of a protease.

[Sequence Listing Free Text]

SEQ ID NOs: 9 to 32 and 37: synthetic peptides

SEQ ID NOs: 33 to 36, 38, and 39: synthetic DNA

The invention claimed is:

1. A recombinant activin A, comprising a modified proregion, wherein the modified proregion comprises an amino acid sequence selected from the group consisting of (a), (b) and (d):
  (a) an amino acid sequence in which an amino acid sequence from position 182 to 199 of the amino acid sequence of SEQ ID NOs: 4, 5 or 6 is deleted;
  (b) an amino acid sequence in which an amino acid sequence from position 182 to 199 of the amino acid sequence of SEQ ID NOs: 4, 5 or 6 is substituted with a spacer sequence consisting of 1 to 10 amino acids; and
  (d) an amino acid sequence in which a least one of amino acids from position 180 to 201 of the amino acid sequence of SEQ ID NOs: 4, 5, or 6 has at least one amino acid inserted therein.

2. The recombinant activin A according to claim 1, wherein the amino acid constituting the spacer sequence in the amino acid sequence (b) is at least one amino acid selected from the group consisting of glycine, alanine, and serine.

3. The recombinant activin A according to claim 1, wherein the recombinant activin A has resistance to degradation by a protease other than Furin.

4. A recombinant activin A, comprising a modified proregion, wherein the modified proregion comprises an amino acid sequences selected from the group consisting of (e) to (g):
  (e) an amino acid sequence selected from the group consisting of the amino acid sequence of SEQ ID NOs: 9 to 20;
  (f) an amino acid sequence in which at least one amino acid is deleted, substituted or added in an amino acid sequence selected from the group consisting of the amino acid sequence of SEQ ID NOs: 9 to 20, wherein the recombinant activin A whose proregion is modified so that it has resistance to degradation by a protease other than Furin; and
  (g) an amino acid sequence having at least 80% homology with an amino acid sequence selected from the group consisting of the amino acid sequence of SEQ ID NOs: 9 to 20, wherein the recombinant activin A comprising the amino acid sequence has resistance to degradation by a protease other than Furin.

5. A polynucleotide encoding the recombinant activin A according to claim 1 or 4.

6. A vector comprising the polynucleotide according to claim 5.

7. A transformant expressing the recombinant activin A according to claim 1 or 4.

8. The transformant according to claim 7, wherein the transformant is a plant transformant.

9. The transformant according to claim 8, wherein the transformant expresses the recombinant activin A in apoplast.

10. A method for producing a recombinant activin A, the method comprising:
  recovering the recombinant activin A expressed in the transformant according to claim 7.

11. A method for producing a recombinant activin A, the method comprising:
  (a) recovering the recombinant activin A expressed in the transformant according to claim 7; and
  (b) treating the obtained recombinant activin A with Furin.

12. A mixture comprising:
  (i) a recombinant activin A comprising a modified proregion and
  (ii) a recombinant mature activin A,
  wherein the modified proregion comprises an amino acid sequence selected from the group consisting of (a), (b), and (d):
  (a) an amino acid sequence in which an amino acid sequence from position 182 to 199 of the amino acid sequence of SEQ ID NOs: 4, 5, or 6 is deleted;
  (b) an amino acid sequence in which an amino acid sequence from position 182 to 199 of the amino acid sequence of SEQ ID NOs: 4, 5, or 6 is substituted with a spacer sequence consisting of 1 to 10 amino acids; and
  (d) an amino acid sequence in which an amino acid sequence from position 180 to 201 of the amino acid sequence of SEQ ID NOs: 4, 5, or 6 has at least one amino acid inserted therein.

* * * * *